(12) United States Patent
Lee et al.

(10) Patent No.: US 11,403,983 B2
(45) Date of Patent: Aug. 2, 2022

(54) DISPLAY CONTROLLER, DISPLAY SYSTEM INCLUDING THE DISPLAY CONTROLLER, AND METHOD OF OPERATING THE DISPLAY CONTROLLER

(71) Applicant: SAMSUNG ELECTRONICS CO., LTD., Suwon-si (KR)

(72) Inventors: Changju Lee, Suwon-si (KR); Yoonkyung Choi, Seoul (KR); Jinbong Kim, Yongin-si (KR); Junho Huh, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/996,391

(22) Filed: Aug. 18, 2020

(65) Prior Publication Data

US 2021/0065602 A1   Mar. 4, 2021

(30) Foreign Application Priority Data

Sep. 2, 2019 (KR) .................. 10-2019-0108470
Dec. 11, 2019 (KR) .................. 10-2019-0164797

(51) Int. Cl.
*G06F 3/041* (2006.01)
*G06V 40/13* (2022.01)
(Continued)

(52) U.S. Cl.
CPC ............. *G09G 3/20* (2013.01); *A61B 5/6898* (2013.01); *G06F 3/0412* (2013.01); *G06F 3/0416* (2013.01); *G06V 40/1318* (2022.01); *G06F 1/3265* (2013.01); *G09G 2310/0275* (2013.01); *G09G 2310/0278* (2013.01); *G09G 2310/08* (2013.01); *G09G 2330/023* (2013.01); *G09G 2370/08* (2013.01)

(58) Field of Classification Search
None
See application file for complete search history.

(56) References Cited

U.S. PATENT DOCUMENTS 9,665,785 B2   5/2017 Han et al.
9,678,586 B2   6/2017 Reynolds
(Continued)

FOREIGN PATENT DOCUMENTS

KR           101590384 B1   2/2016
KR      1020190074776 A   6/2019

*Primary Examiner* — Duane N Taylor, Jr.
(74) *Attorney, Agent, or Firm* — Sughrue Mion, PLLC

(57) ABSTRACT

A display chipset structure that is based on an integrated display controller is provided. The display controller includes including a display processor comprising a first digital circuit, and configured to receive image data from an application processor (AP) and output the image data to a first component driver chip configured to drive a gate line and a source line of a display panel; and a touch processor comprising a second digital circuit, and configured to receive touch data from a second component driver chip configured to drive sensing electrodes of a touch panel. The display controller is implemented as one semiconductor chip and separated from each of the first and second component driver chips, and the display processor and the touch processor communicate with each other through an internal interconnection of the one semiconductor chip.

19 Claims, 17 Drawing Sheets

(51) Int. Cl.
    *G06K 9/00*     (2006.01)
    *A61B 5/00*     (2006.01)
    *G09G 3/20*     (2006.01)
    *G06F 1/3234*     (2019.01)

(56) References Cited

U.S. PATENT DOCUMENTS

| | | |
|---|---|---|
| 2014/0362031 A1 | 12/2014 | Mo et al. |
| 2016/0162116 A1 | 6/2016 | Kuge et al. |
| 2017/0220201 A1 | 8/2017 | Ludwig |
| 2018/0012069 A1* | 1/2018 | Chung ................ G06K 9/2036 |
| 2018/0074627 A1* | 3/2018 | Kong ................ G06K 9/00013 |
| 2019/0130157 A1 | 5/2019 | Oh |
| 2019/0147800 A1 | 5/2019 | Bae et al. |
| 2021/0056333 A1* | 2/2021 | Cheng ................ G06K 9/0004 |

* cited by examiner

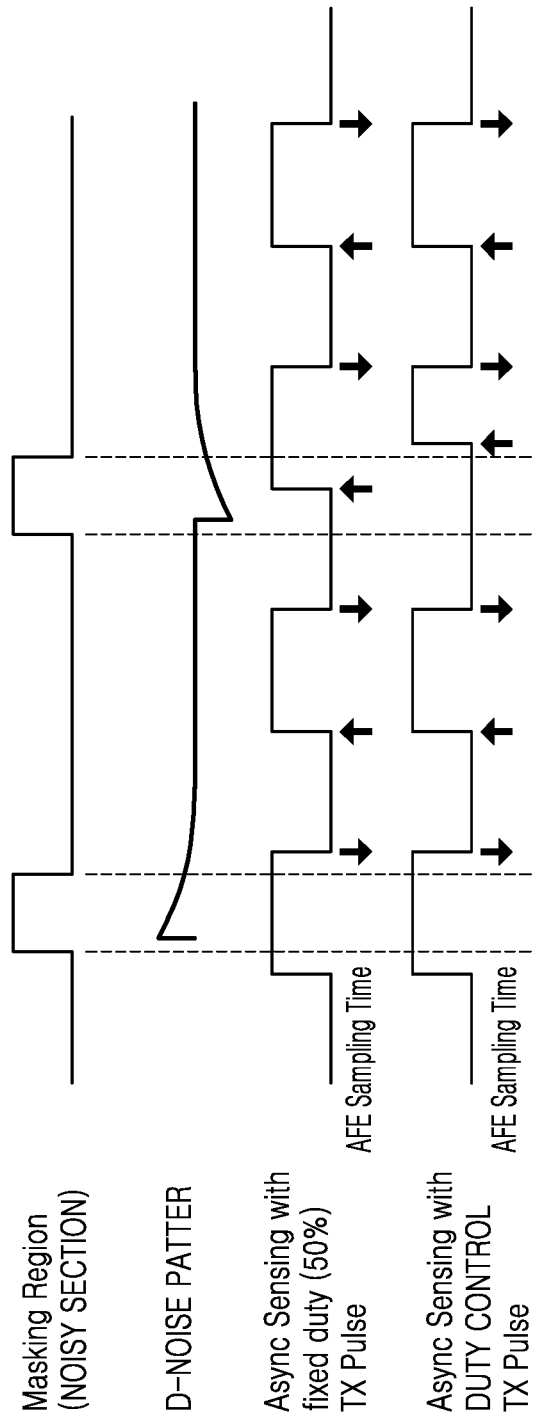

DISPLAY CONTROLLER, DISPLAY SYSTEM INCLUDING THE DISPLAY CONTROLLER, AND METHOD OF OPERATING THE DISPLAY CONTROLLER

CROSS-REFERENCE TO RELATED APPLICATIONS

This application is based on and claims priority to Korean Patent Applications Nos. 10-2019-0108470 and 10-2019-0164797, respectively filed on Sep. 2, 2019 and Dec. 11, 2019, in the Korean Intellectual Property Office, the disclosures of which are incorporated by reference herein in their entireties.

BACKGROUND

1. Field

Example embodiments of the disclosure relate to a display controller, and more particularly, to a display controller, a display system including the display controller, and a method of operating the display controller.

2. Description of Related Art

In recent years, a display device is not only configured to embody a screen, but also to embody various other functions and components, such as a touch sensor, display fingerprint recognition (e.g., Fingerprint on Display (FoD)), a bio-sensor, a force sensor, and an under display camera (UDC). As an example, components for the above-described functions and separate chips configured to control the components may be embodied and assembled into the display device. However, as display devices become thinner and larger, interference between the components may be increased. Thus, it is highly likely that the performance of a display device configured to provide various functions may be degraded.

SUMMARY

One or more example embodiments provide a display chipset structure, which is based on an integrated display controller, and provide a display controller that improves the performance of various functions, a display system including the display controller, and a method of operating the display controller.

According to an embodiment, there is provided a display controller including a display processor comprising a first digital circuit, and configured to receive image data from an application processor (AP) and output the image data to a first component driver chip configured to drive a gate line and a source line of a display panel; and a touch processor comprising a second digital circuit, and configured to receive touch data from a second component driver chip configured to drive sensing electrodes of a touch panel. The display controller is implemented as one semiconductor chip and separated from each of the first and second component driver chips, and the display processor and the touch processor communicate with each other through an internal interconnection of the one semiconductor chip.

The display processor further includes a timing controller configured to output one or more synchronous signals to the first component driver chip, and timing information based on at least one synchronous signal among the one or more synchronous signals is provided to the touch processor.

The touch processor is further configured to generate a timing control signal based on the timing information, and transmit the timing control signal to the second component driver chip to control a time point at which the touch data is generated.

The display controller further includes a fingerprint processor including a third digital circuit configured to perform a fingerprint recognition function, the fingerprint processor being configured to control a third component driver chip to generate a fingerprint image and configured to drive a fingerprint sensor.

The display controller further includes a bio-signal processor including a fourth digital circuit configured to perform a bio-signal sensing function, the bio-signal processor being configured to control a sensing operation of a fourth component driver chip. The fourth component driver chip is configured to drive a bio-signal sensor.

The display processor includes a frame memory configured to store image data to be displayed on the display panel; and an image processing circuit configured to perform an image processing operation on the image data.

The display processor is configured to transmit a control signal to the first component driver chip when the first component driver chip is in a low-power mode, and a power generator included in the first component driver chip supplies power to the second component driver chip to periodically perform the touch sensing operation.

The touch processor further includes a memory configured to store the touch data received from the second component driver chip; and a touch position calculator configured to calculate a touch position based on information stored in the memory.

According to an embodiment, there is provided a method of operating a display controller. The method including receiving, by a second digital circuit included in the display controller, touch data obtained from a second component driver chip and controlling the second component driver chip to drive sensing electrodes of a touch panel; controlling, by a first digital circuit included in the display controller, a first component driver chip to drive a pixel of a display panel for a fingerprint sensing operation; receiving a fingerprint image from a third component driver chip that is configured to drive a fingerprint sensor; transmitting a first control signal for waking up an application processor (AP) that is in a low-power mode, to the application processor; and transmitting the fingerprint image to the application processor for a fingerprint authentication operation. The display controller is implemented as one semiconductor chip and separated from each of the first, second and third component driver chips.

The first component driver chip and the second component driver chip are in a low-power mode. The method further includes outputting a second control signal for waking up the first component driver chip and the second component driver chip based on the received touch data.

The method further includes determining whether the touch data indicates a touch of a user for the fingerprint sensing operation, wherein the transmitting the first control signal to the application processor further includes selectively transmitting the first control signal based on the touch data indicating the touch of the user for the fingerprint sensing operation.

The method further includes outputting a third control signal configured to drive the first component driver chip and the second component driver chip to enter a low-power mode based on determining that the touch data does not indicate the touch of the user for the fingerprint sensing operation.

The method further includes transmitting at least one piece of timing information related to a display operation from the first digital circuit to the second digital circuit; and outputting, from the second digital circuit, a timing control signal for controlling a time point at which the touch data is generated by the second component driver chip.

The method further includes communicating with the first component driver chip and the second component driver chip according to a first interface; and communicating with the application processor according to a second interface, where the first interface is different from the second interface.

According to an embodiment, there is provided a display system including: a display panel; a touch panel; a plurality of component driver circuits comprising a display driver configured to drive the display panel and a touch controller configured to drive the touch panel, the display driver and the touch controller including analog circuits; and a display controller implemented as a separate chip between the plurality of component driver circuits and an application processor (AP), the display controller comprising a first digital circuit configured to control the display driver and a second digital circuit configured to control the touch controller. The display controller is configured to transmit image data for displaying an image on the display panel to a source driver included in the display driver.

The display controller is further configured to receive touch data from the touch controller comprising an analog front end (AFE), wherein the touch data is based on a result of the driving of the touch panel.

The first digital circuit is configured to transmit at least one piece of timing information related to a display operation to the second digital circuit, and the second digital circuit is configured to generate a timing control signal for controlling a time point at which touch data is generated by the touch controller.

The display system further includes a mainboard and a display module board, where the application processor is mounted on the mainboard, and the plurality of component driver circuits and the display controller are mounted on the display module board.

The display driver includes a power generator configured to generate power for a display operation and a touch sensing operation, and when the display driver is in a low-power mode, the power generator provides power to the touch controller so that the touch controller periodically performs the touch sensing operation.

The display system further includes a fingerprint sensor, where the plurality of component driver circuits further include a fingerprint controller configured to drive the fingerprint sensor, and the display controller further comprises a third digital circuit configured to control the fingerprint controller. The display controller controls an operation of generating a fingerprint image without waking up the application processor that is in a low-power mode.

BRIEF DESCRIPTION OF THE DRAWINGS

The above and other aspects, features, and advantages of certain example embodiments will be more apparent from the following description taken in conjunction with the accompanying drawings, in which:

FIGS. 7A to 7C are diagrams illustrating examples of reducing interference between a display operation and a touch sensing operation according to example embodiments;

FIG. 11($b$) is a diagram illustrating an example operation of a display system according to an example embodiment;

DETAILED DESCRIPTION

Hereinafter, embodiments will be described in detail with reference to the accompanying drawings.

Figure 1:
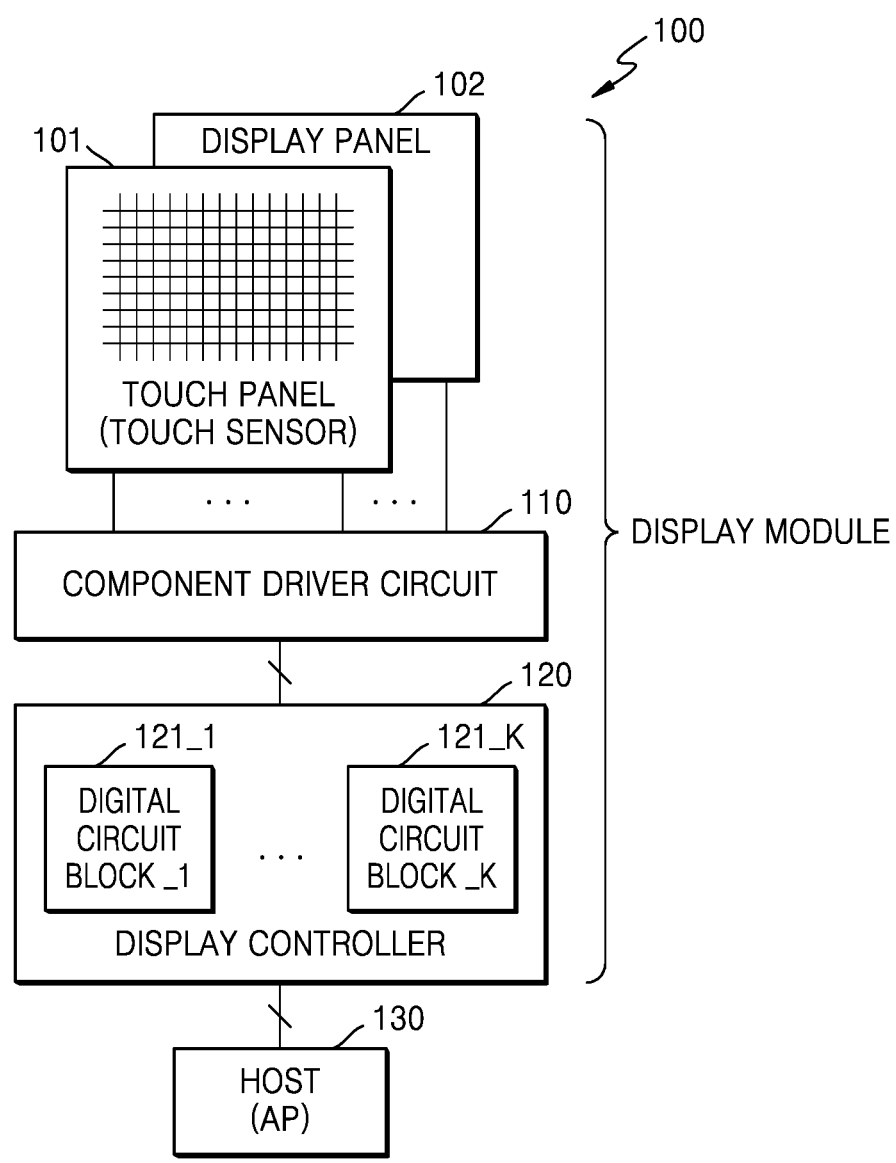
FIG. 1 is a block diagram illustrating a display system according to an example embodiment.

FIG. 1 is a block diagram of a display system 100 according to an example embodiment.

Referring to FIG. 1, the display system 100 may include components configured to perform various functions, such as a display function, a touch sensing function, and a finger recognition function. As an example, the display system 100 may include a touch panel 101 and a display panel 102. The touch panel 101 may include a plurality of sensing electrodes configured to provide sensing signals based on various touch sensing methods. As an example, the sensing electrodes may provide a sensing signal based on a capacitive touch method or provide a sensing signal based on a pressure touch method.

The display system 100 may be mounted on various electronic devices. For example, the display system 100 may be mounted on electronic devices, such as a personal computer (PC), a network server, a tablet PC, an electronic reader (e-reader), a personal digital assistant (PDA), a portable multimedia player (PMP), a mobile phone, a smartphone, a wearable device, an Internet of Things (IoT) device, a refrigerator, and a navigation device. Also, the display system 100 may be mounted on an electronic device, which is included as a component in vehicles, furniture, manufacturing equipment, doors, and various measuring devices.

In FIG. 1, the touch panel 101 and the display panel 102 are illustrated as separate components, but embodiments are not limited thereto. For example, the touch panel 101 may be implemented as an in-cell-type panel in which the sensing electrodes are combined with a display pixel. In this case, the sensing electrodes of the touch panel 101 may include at least one element included in the display pixel, for example, one of a source drive line, a gate line, an anode pixel electrode, and a cathode pixel electrode. Alternatively, the plurality of sensing electrodes may be common sources to which a display common voltage is applied.

Alternatively, the touch panel 101 may be an on-cell type in which the sensing electrodes are arranged on the display panel 102. In addition, the display panel 102 may include a liquid crystal display (LCD), a light-emitting diode (LED) display, an organic LED (OLED) display, an active-matrix OLED (AMOLED) display, and/or a flexible display. In addition, the display panel 102 may include other types of flat-panel displays.

Moreover, the display system 100 may further include a component driver circuit 110 and a display controller 120. Although FIG. 1 illustrates an example in which the display system 100 further includes a host 130, the host 130 may be a subject that is located outside the display system 100 and communicates with the display system 100.

The display system 100 used in recent mobile devices, such as a smartphone or a foldable phone, may be made thinner and larger to increase a display form factor or a battery space. As such, various types of components may be located in relatively close contact with each other. As a result, interferences between the components may gradually increase. As an example, the display system 100 may include the touch panel 101, the display panel 102, and other circuits configured to drive the touch panel 101 and the display panel 102. For example, when an interference between the touch panel 101 and the display panel 102 is increased, the performance of a display operation that embodies a screen may be degraded, or the performance of an operation related to touch recognition may be degraded.

As an example, analog circuits and digital circuits may be provided to drive and control each of the components disposed in the display system 100. For example, analog circuits may be configured to drive the sensing electrodes in relation to the touch panel 101 and digital circuits may be configured to calculate touch positions using touch data. In addition, analog circuits configured to drive gate lines and source lines (or data lines) in relation to the display panel 102 and digital circuits configured to perform various processes of, for example, storing image data and improving image quality, may be provided.

The component driver circuit 110 may include analog circuits configured to drive a display device including the touch panel 101 and the display panel 102 and drive various other kinds of components. For example, the component driver circuit 110 may include analog circuits configured to provide a touch function, a display function, a fingerprint recognition function, and a bio sensing function. According to an embodiment, a separate semiconductor chip (e.g., a component driver chip) may be implemented to control each of various components. Each component driver chip may include analog circuits configured to drive a component corresponding thereto. For example, a touch sensing-related chip (e.g., a touch driver chip) included in the component driver circuit 110 may provide driving signals to the sensing electrodes of the touch panel 101 and receive the sensing signals from the sensing electrodes. In addition, a display driving-related chip (e.g., a display driver chip) included in the component driver circuit 110 may include a driver configured to drive gate lines and source lines of the display panel 102.

Moreover, the display controller 120 may be implemented as one chip, and circuits configured to control various components may be integrated in the display controller 120. As an example, digital circuits corresponding to component driver chips for various components having a touch function, a display function, a fingerprint recognition function, and a bio-signal sensing function may be integrated in the display controller 120. As an example, FIG. 1 illustrates an example in which the display controller 120 includes first to K-th digital circuit blocks 121_1 to 121_K. Each of the first to K-th digital circuit blocks 121_1 to 121_K may include digital circuits configured to control a component driver chip corresponding thereto.

The host 130 may perform the overall control operation on the display system 100. For example, the host 130 may generate and provide data related to a display operation. In addition, the host 130 may receive a touch recognition result and perform various control operations based on the touch recognition result. In addition, the host 130 may perform the overall control operation on various functions (e.g., a fingerprint sensing function and a bio-sensing function), which are applicable to the display system 100. For example, the host 130 may include an application processor (AP), which may be implemented as a System on Chip (SoC). The SoC may include a system bus to which a protocol having predetermined standard bus specifications is applied. Various kinds of specifications, such as an advanced microcontroller bus architecture (AMBA) protocol (available from Advanced RISC Machine (ARM)), may be applied as a standard specification of the system bus. When a modem function is embedded in the AP, the AP may be also referred to as ModAP.

According to an example embodiment, at least one of the first to K-th digital circuit blocks 121_1 to 121_K of the display controller 120 may communicate with another digital circuit block of the display controller 120. Thus, various pieces of information required for reducing interference between components may be transmitted and received among the first to K-th digital circuit blocks 121_1 to 121_K. For example, a digital circuit block related to a display operation may determine time points at which various voltage signals provided to the display panel 102 fluctuate. At least one piece of timing information may be provided to a digital circuit block related to a touch sensing operation to prevent the performance of a touch recognition result from being degraded due to the fluctuation of the voltage signals.

Furthermore, according to an example embodiment, the display controller 120 may further include a processor or controller configured to control the first to K-th digital circuit blocks 121_1 to 121_K. That is, an operation of each of the first to K-th digital circuit blocks 121_1 to 121_K may be controlled by the processor.

FIG. 1 illustrates an embodiment in which the component driver circuit 110 includes analog circuits, and the display controller 120 includes digital circuits, but the display system 100 according to embodiments may be variously modified. As an example, the display system 100 may include analog circuits and digital circuits in relation to various functions of the display system 100. In addition, the component driver circuit 110 may also include some digital circuits, and the display controller 120 may include some analog circuits.

Moreover, components and chips may be mounted on a module board in the display system 100, and configurations included in the module board may be referred to as a display module. In example embodiments, the display module may include components, the component driver circuit 110, and the display controller 120.

Figure 2:
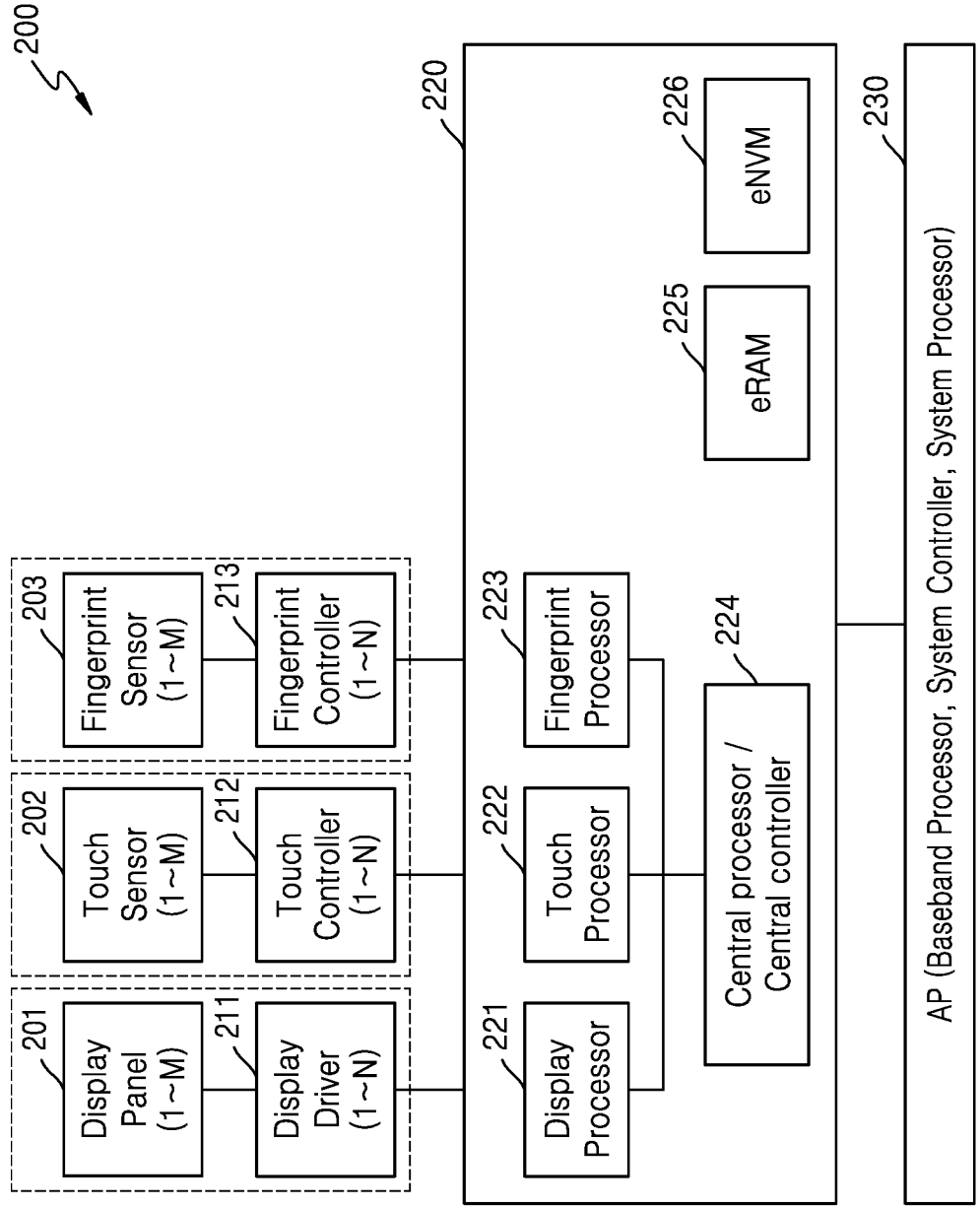
FIGS. 2 and 3 are block diagrams illustrating a display system according to example embodiments.
Figure 3:
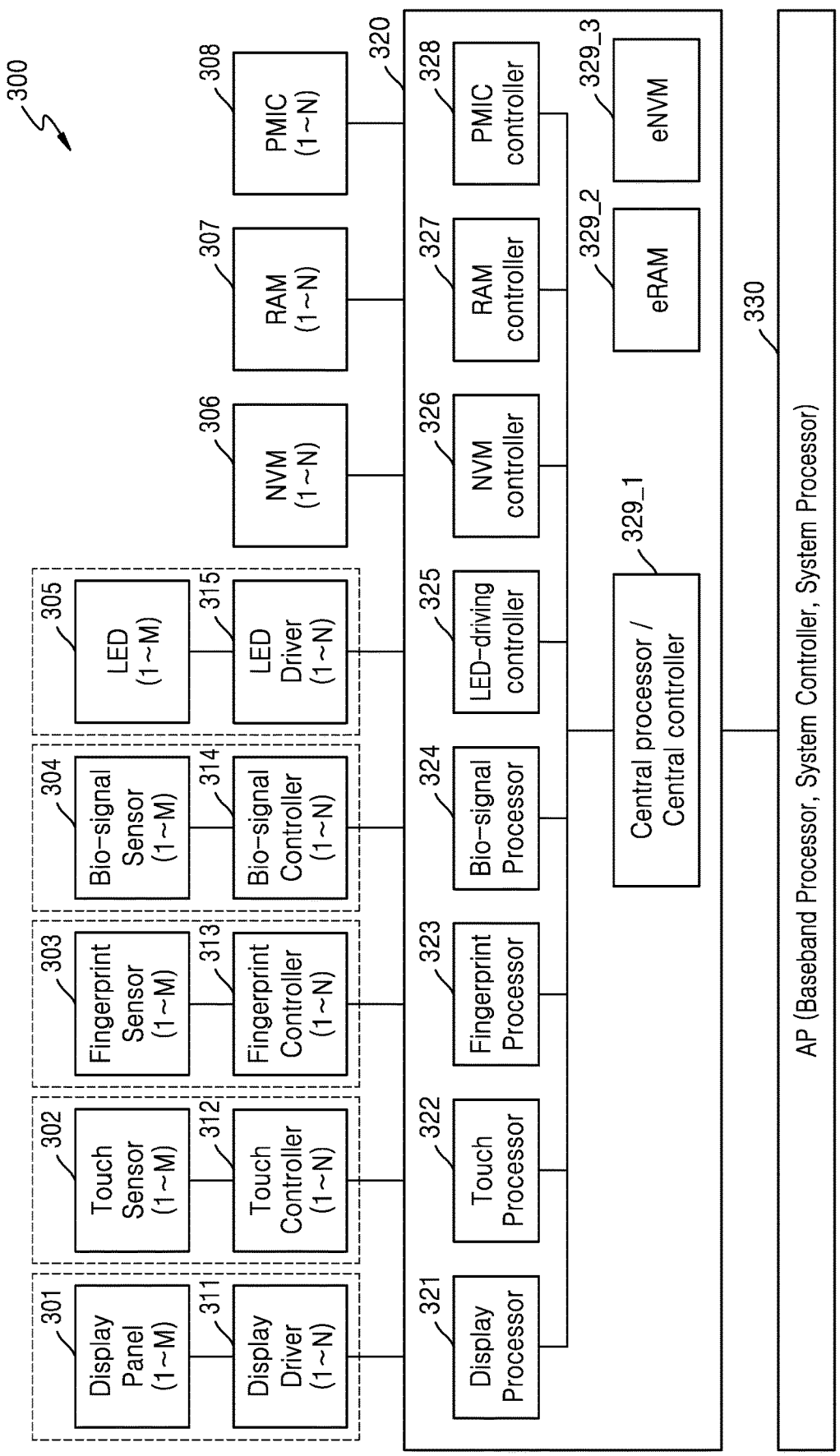

FIGS. 2 and 3 are block diagrams of a display system 200 according to example embodiments.

In a typical chipset structure, a plurality of chips related to various functions of the display system may be separately arranged. The plurality of chips may be directly connected to a main system processor (e.g., an AP) and controlled by the main system processor. In contrast, according to an example embodiment as shown in FIG. 2, a display controller (or a display processor) configured to integrate and manage components may be between the main system processor and the components. As an example, the display system 200 may include a display panel 201, a touch sensor 202, and a fingerprint sensor 203 as components and further include a display driver 211, a touch controller 212, and a fingerprint controller 213 as component driver circuits configured to drive the components. The display driver 211, the touch controller 212, and the fingerprint controller 213 may each include separate component driver chips. Also, the touch sensor 202 may correspond to the touch panel according to the above-described embodiment.

In addition, the display system 200 may further include a display controller 220 and an AP 230. The display controller 220 may include various kinds of digital circuit blocks configured to manage components. According to an embodiment, the display controller 220 may include a display processor 221, a touch processor 222, and a fingerprint processor 223. The display controller 220 may further include a central processor (or central controller) 224 and at least one memory, for example, an embedded RAM (eRAM) 225 and an embedded non-volatile memory (eNVM) 226.

The display controller 220 may control each of the components (or the component driver chips) and various functions for linking operation between the components. For example, each of the display processor 221, the touch processor 222, and the fingerprint processor 223 included in the display controller 220 may communicate with a component driver chip corresponding thereto. That is, the display processor 221 may communicate with the display driver 211 to control the display panel 201, the touch processor 222 may communicate with the touch controller 212 to control the touch sensor 202, and the fingerprint processor 223 may communicate with the fingerprint controller 213 to control the fingerprint sensor 203. Also, the display processor 221, the touch processor 222, and the fingerprint processor 223 may be connected to each other through internal interconnections to share at least one signal. In addition, a mutual operation between the components included in the display controller 220 may be controlled by the central processor 224.

Moreover, FIG. 3 illustrates an example in which a display system 300 includes various other components. According to an embodiment, the display system 300 may include a display panel 301, a touch sensor 302, a fingerprint sensor 303, a bio-signal sensor 304, and an LED 305. The display system 300 may further include a display driver 311, a touch controller 312, a fingerprint controller 313, a bio-signal controller 314, and an LED driver 315, which are configured to drive or control the corresponding components described above, respectively.

In addition, the display system 300 may further include at least one memory and power management components. As an example, the display system 300 may further include a non-volatile memory (NVM) 306, a RAM 307, and a power management integrated circuit (PMIC) 308. The NVM 306, the RAM 307, and the PMIC 308 may be directly controlled by a display controller 320. Thus, the NVM 306, the RAM 307, and the PMIC 308 may be designated as components or component driver chips. That is, in some embodiments, the display controller 320 may directly communicate with the NVM 306, the RAM 307, and the PMIC 308.

Furthermore, the display controller 320 may include a display processor 321, a touch processor 322, a fingerprint processor 323, a bio-signal processor 324, an LED-driving controller 325, an NVM controller 326, a RAM controller 327, and a PMIC controller 328 that correspond to the above-described components (or component driver chips). The display system 300 may include various other kinds of components, which may be applicable to the display system 300. As described above, driving and/or control operations of the components may be performed based on communication between the component driver chips and the display controller 320.

According to an embodiment, the display controller 320 may further include a central processor 329_1 and at least one memory, for example, an eRAM 329_2 and an eNVM 329_3. The display system 300 may further include an AP 330.

As an operation example, the display system 300 may recognize a user's fingerprint according to various methods. When a fingerprint is recognized using an optical method, the fingerprint sensor 303 may include an image sensor configured to print or capture an image of the fingerprint. The fingerprint controller 313 may include various analog circuits configured to drive the image sensor, and the fingerprint processor 323 may include digital circuits configured to perform various operations (e.g., an image filtering operation) on an image of a fingerprint.

Furthermore, the bio-signal sensor 304 may be configured to detect various bio-signals indicating, for example, user's body characteristics, and the LED 305 may be configured to emit light having a predetermined frequency range. For example, when the bio-signals are generated using an optical method, the bio-signal sensor 304 may use light emitted by the LED 305. Also, the bio-signal controller 314 and the LED driver 315 may respectively drive the bio-signal sensor 304 and the LED 305. The bio-signal processor 324 may perform a digital processing operation on information from the bio-signal controller 314, and the LED-driving controller 325 may perform various kinds of digital processing operations for controlling the LED driver 315.

In FIGS. 2 and 3, each block illustrated with a dashed line may indicate that a component is integrally formed with a component driver circuit corresponding thereto. However, the component may be located separately from the component driver circuit corresponding thereto. As an example, a display panel may be formed by integrating a display driver with a display panel configured to output an actual image. Alternatively, the display driver may be implemented as a separate component driver chip, and the component driver chip may be mounted on the display panel. FIGS. 2 and 3 illustrate embodiments in which a plurality of components may be simultaneously used to serve the same function among a plurality of functions. Therefore, the components may be connected to and combined with the component driver circuits not only on a one-to-one basis, but also on a one-to-n or m-to-n basis (where m and n are positive integers). According to embodiments, a plurality of components and a plurality of component driver circuits corresponding thereto may be arranged in relation to any one function. For example, the display system 300 may include at least two display panels, and a plurality of component driver circuits may be arranged to correspond to each of the display panels.

The display system according to the above-described embodiments may produce various effects. For example, it may reduce an interference between a display panel and a touch sensor. In a display chipset structure of the related art, interference between the display panel and the touch sensor may be increased due to the ultra-thinning and scaling-up of displays. Because a plurality of chips configured to control components are implemented separately from each other, information may not be shared among the chips, the complexity in designing interconnections between the chips to share information may be increased, or manufacturing costs may be increased.

In contrast, according to example embodiments, digital circuits for various functions may be integrated in a display controller that is implemented as one chip, and information may be easily shared among the digital circuits. As an example, in relation to a display operation and a touch sensing operation, a display driver and a touch controller may be controlled so that a fluctuation amount of a common source may be minimized at a time point at which a display signal is stored or a touch signal is sampled. Here, most touch sensors may include a sample-and-hold sensing circuit. As a result, display performance and touch sensing performance may be improved by reducing the above-described interference.

Moreover, although terms, such as a driver, a controller, and a processor, have been used to clearly describe the embodiments above with reference to FIGS. 2 and 3, configurations and functions of the components according to embodiments may not be limited in scope by the terms. That is, each of the components described in the embodiments shown in FIGS. 2 and 3 may be implemented in various forms within a range in which a function of a module corresponding thereto may be realized, and a term for each of the components may also be variously defined. As an example, a display controller described in the above embodiments may be referred to as a display processor.

Figure 4A:
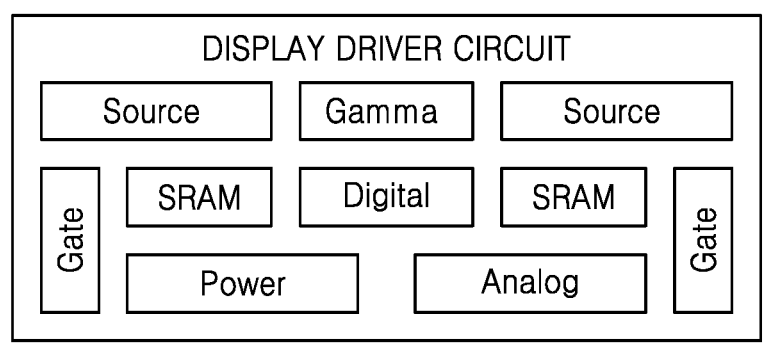
FIGS. 4A-4B and FIGS. 5A-5B are block diagrams illustrating analog circuits and digital circuits configured to control components of a display system according to example embodiments.
Figure 4B:
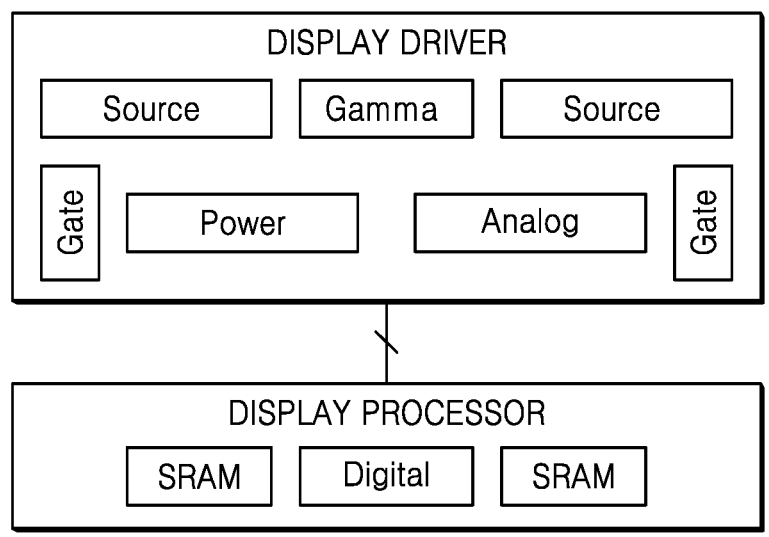
Figure 5A:
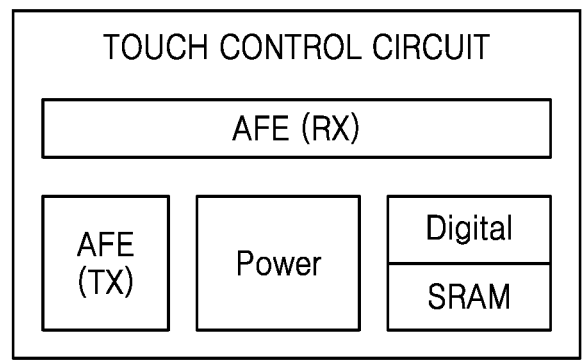
Figure 5B:
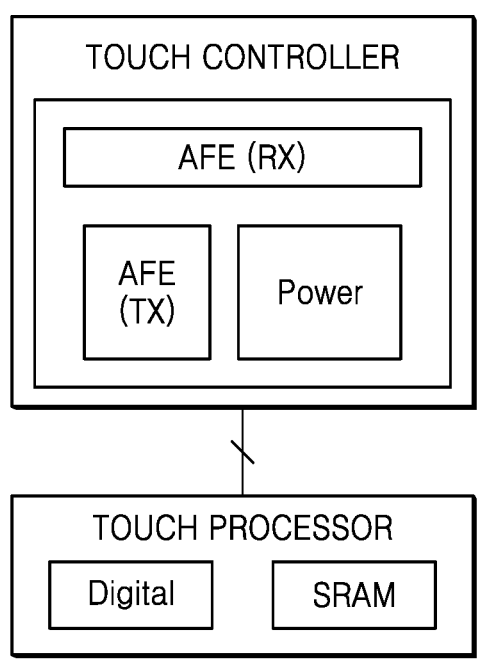

FIGS. 4A-4B and 5A-5B are block diagrams illustrating examples of analog circuits and digital circuits configured to control components according to example embodiments. Specifically, FIGS. 4A and 4B illustrate circuits configured to control a display panel according to example embodiments. FIGS. 5A and 5B illustrate circuits configured to control a touch panel according to example embodiments.

Referring to FIGS. 4A and 4B, a display driver circuit including a plurality of circuit blocks may be configured to control the display panel. Referring to FIG. 4A, the display driver circuit may include a source driver (Source), a gamma circuit (Gamma), a gate driver (Gate), a power control circuit (Power), and other analog circuits (Analog) (or analog circuit blocks). Here, the display driver circuit may also include a memory (e.g., static random access memory (SRAM)) and other digital circuits (Digital) (or digital circuit blocks) according to an embodiment. In general, in the display driver circuit, the areas occupied by the analog circuits may be larger than the areas occupied by the digital circuits. Even when the display driver circuit includes a high-capacity memory, a ratio of the areas of the digital circuits may not likely exceed 50% of the total area of the display driver circuit. Thus, even when the process shrinkage is applied to the digital circuit, there may be a limit as to reducing the total area of the display driver circuit.

According to another example embodiment, referring to FIG. 4B, a display driver corresponding to a component driver circuit may include the analog circuit blocks, from among the components shown in FIG. 4A. That is, the display driver may include a source driver (Source), a gamma circuit (Gamma), a gate driver (Gate), a power control circuit (Power), and other analog circuits (Analog). In addition, a display processor included in a display controller may include the digital circuit blocks, from among the components shown in FIG. 4A. That is, the display processor may include a memory (e.g., SRAM) and other digital circuits (Digital).

Referring to FIG. 5A, a touch control circuit may include circuit blocks configured to control the touch panel. The touch control circuit may include an analog front end receiving block AFE (RX), an analog front end transmission block AFE (TX), and a power control circuit (Power). The touch control circuit may also include a memory (e.g., SRAM) and other digital circuits (Digital) according to an embodiment. In general, in the touch control circuit, the areas occupied by analog circuits may be larger than the areas occupied by digital circuits, and a ratio of the areas of the digital circuits may not likely exceed 30% of the total area of the touch control circuit.

According to another embodiment, referring to FIG. 5B, a touch controller may include the AFE receiving block AFE (RX), the AFE transmission block AFE (TX), and the power control circuit (Power) as the analog circuit blocks, from among the components shown in FIG. 5A. In addition, a touch processor included in the display controller may include the memory (e.g., SRAM) and the other digital circuits (Digital), from among the components shown in FIG. 5A.

According to the above-described embodiments shown in FIGS. 4A, 4B, 5A, and 5B, the digital circuits configured to control various components of a display system may be integrated in the display controller, which corresponds to an integrated display controller chip. Thus, interference between the components may be reduced due to communication between the integrated digital circuits. Also, when the digital circuits included in the display controller are implemented, manufacturing costs may be reduced by applying the process shrinkage.

Moreover, in the above-described embodiment, the display driver and the touch controller may further include various other kinds of analog circuits. As an example, each of the display driver and/or the touch controller may include a high-speed interface configured to receive image data, a low-speed interface configured to receive a control signal from the display controller, a line data buffer (e.g., a latch, a flip-flop, and the like) configured to drive a source line, a special function register (SFR) configured to set a driving mode, and a low-speed interface (e.g., SPI, I2C, I3C, . . . ) configured to transmit touch data to the display controller.

Figure 6:
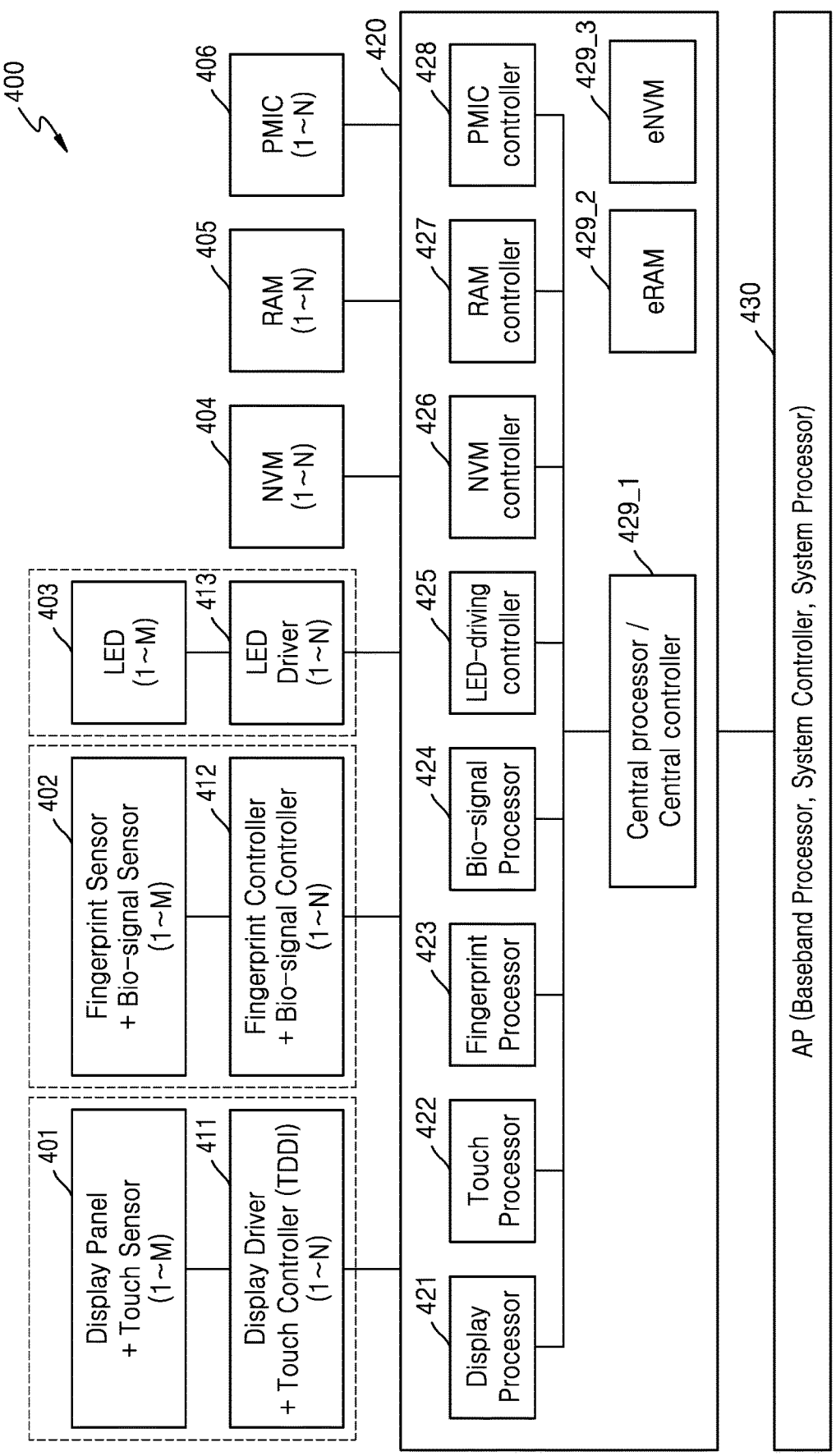
FIG. 6 is a block diagram illustrating a display system according to another example embodiment.

FIG. 6 is a block diagram illustrating a display system 400 according to another example embodiment. The components described in the above-described embodiments may be connected to a driver and a controller, which are configured to control the components in various manners. FIG. 6 illustrates an example in which functions of components included in the display system 400 may be integrated in arbitrary combinations or separated from each other. According to various embodiments, the functions of the components included in the display system 400 may be integrated or separated in other manners in addition to the configuration shown in FIG. 6. FIG. 6 illustrates an example in which a display panel is integrated with a touch sensor, and a fingerprint sensor is integrated with a bio-signal sensor.

Referring to FIG. 6, the display system 400 may include a display panel/touch sensor 401, a fingerprint sensor/bio-signal sensor 402, and an LED 403, and may further include a display driver/touch controller 411, a fingerprint controller/bio-signal controller 412, and an LED driver 413, which correspond thereto. According to the above-described embodiments, the display system 400 may further include an NVM 404, a RAM 405, and a PMIC 406. The display driver/touch controller 411 may be referred to as a touch display driver IC (TDDI) because the display driver/touch controller 411 may control both a display operation and a touch sensing operation. In addition, digital circuits configured to process digital signals in relation to the display operation and the touch sensing operation may be configured in a display controller 420.

The display controller 420 according to an example embodiment may be between component driver circuits for various functions and an AP 430. The AP 430 may control components via the display controller 420, and results obtained by driving the components may be provided to the AP 430 via the display controller 420. Also, the display controller 420 may include a display processor 421, a touch processor 422, a fingerprint processor 423, a bio-signal processor 424, an LED driving controller 425, an NVM controller 426, a RAM controller 427, and a PMIC controller 428. In addition, the display controller 420 may further include a central processor 429_1 and at least one memory, for example, an eRAM 429_2 and an eNVM 429_3.

Referring to FIG. 6, analog circuits configured to control various components included in the display system 400 may be variously integrated with or separated from each other according to various operation methods. The display controller 420 may control the analog circuits, which are integrated with or separated from each other. As an example, digital circuit blocks included in the display controller 420 may be connected to each other and share various pieces of information with each other, and the various pieces of information may be shared between the digital circuit blocks to correspond to the integration of the analog circuits. In contrast, when the component driver circuits are separately embodied and independently driven, the display system 400 may be implemented such that each of the digital circuit blocks included in the display controller 420 may control a component driver circuit having a function corresponding thereto.

Figure 7A:
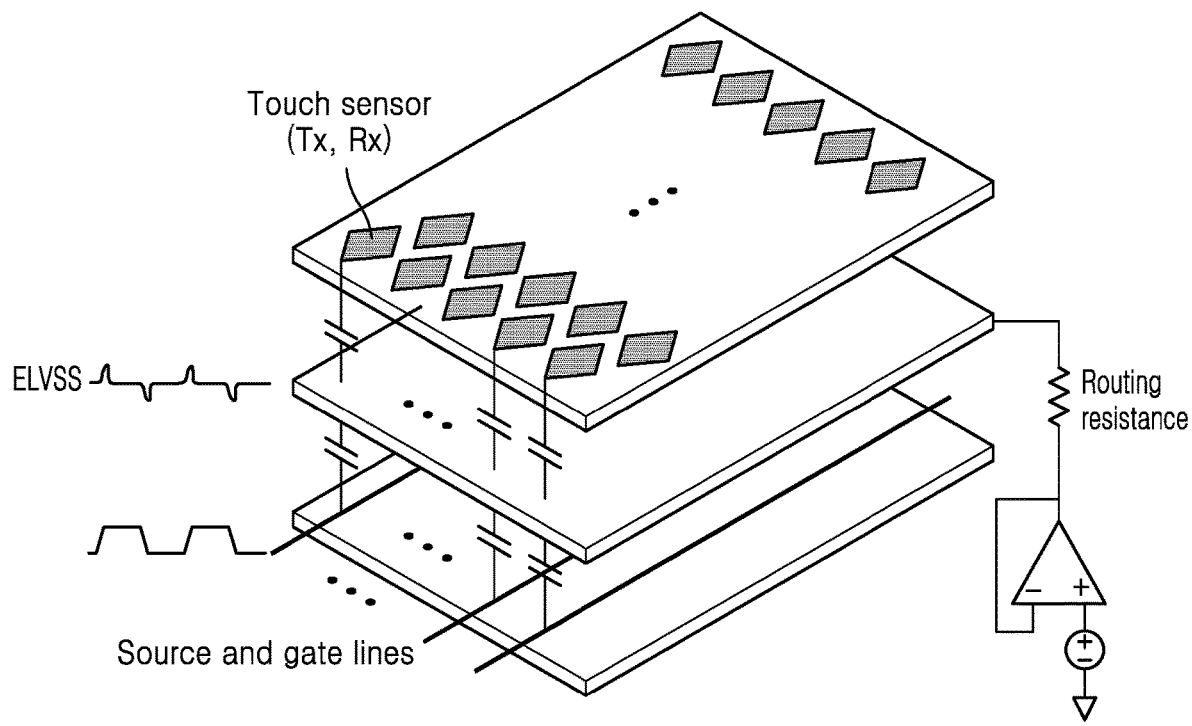
Figure 7B:
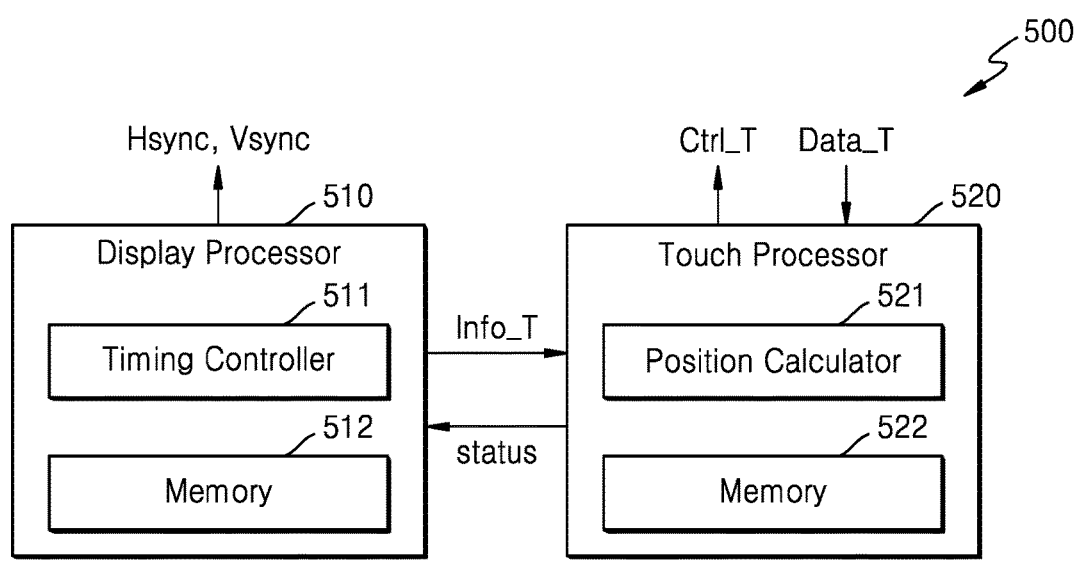

FIGS. 7A to 7C are diagrams illustrating examples of reducing interference between a display operation and a touch sensing operation according to example embodiments. FIGS. 7A to 7C illustrate examples in which a display panel corresponds to an OLED display, and a touch sensor includes sensing electrodes that are arranged on the OLED display.

FIG. 7A illustrates a mechanism of interference between an OLED display and a touch sensor. In the OLED display, a common source (e.g., an ELVSS electrode) corresponding to a ground electrode of the display may be between a display panel and the touch sensor. As the thickness of the display is reduced, capacitance between the common source and a display source line and capacitance between the common source and the touch sensor may be greatly increased. In this case, when an electric potential of the display source line or a gate line toggles, a fluctuation amount of the common source may be increased, and part of a fluctuation signal may be applied to the touch sensor and recognized as noise in a touch signal. Also, high-voltage touch signals driven for a touch sensing operation may also lead to the fluctuation of an electric potential of the common source, and there may be a problem that inaccurate data may be stored in each pixel of the display panel due to the fluctuation of the electric potential of the common source.

According to embodiments, communication may be performed between digital circuit blocks configured to control a display operation and a touch operation in a display controller, and a control operation capable of reducing the interference may be performed based on the communication.

FIG. 7B illustrates a display controller 500 according to an example embodiment. The display controller 500 may include a display processor 510 configured to control a component driver circuit related to a display operation and a touch processor 520 configured to control a component driver circuit related to a touch sensing operation. The display processor 510 may include a timing controller 511 configured to generate various kinds of signals (e.g., a horizontal synchronous signal HSync and a vertical synchronous signal VSync) in relation to the display operation and a memory 512 configured to store frame data in connection with the operation of a screen. Also, the touch processor 520 may include a position calculator 521 and a memory 522. The touch processor 520 may output a touch control signal Ctrl_T to a touch controller and receive touch data Data_T from the touch controller.

Moreover, various pieces of information may be transmitted and received between the display processor 510 and the touch processor 520. As an example, the display processor 510 may detect a drive status of a display panel (e.g., a position of a driven gate line) and detect time points at which various voltages provided to drive the display panel fluctuate. The display processor 510 may provide timing information (Info_T) to the touch processor 520 so that the touch data (Data_T) may be generated at a time point when interference is minimized. The touch processor 520 may provide the touch control signal (Ctrl_T) to the touch controller such that the touch data Data_T may be generated at a time point when interference may be minimized, based on the timing information Info_T.

Moreover, the touch processor 520 may provide status information (Status) including various pieces of information related to a touch operation to the display processor 510. The status information Status may indicate whether the touch processor 520 and analog circuits for a touch sensing operation are in a normal mode or a low-power mode. Also, various types of information, such as a touch sensing frequency, may be included in the status information Status. As an example, a display driver may include a power generator, which may provide power to the touch controller. An operation of providing power to the touch controller may be controlled based on the status information Status.

FIG. 7C is a graph showing an example of controlling a time point (or an AFE sampling time point) at which touch data is generated, according to an example embodiment. Referring to FIG. 7C, a masking region may be variously defined based on a display operation such that touch data is not generated during a section in which noise D-Noise is greatly generated due to a touch sensing operation. According to an example embodiment, a time point at which the touch data is generated may be controlled by adjusting a pulse width of a driving signal TX provided to a touch panel (or a touch sensor). As an example, when the pulse width of the driving signal TX is maintained constant regardless of the display operation, a sampling time point illustrated with arrows may be included in a noise section. However, a situation in which the sampling time points are included in the noise section may be prevented by adjusting the pulse width of the driving signal TX based on timing information Info_T.

According to the above-described example embodiment, a signal for the display operation and a signal for the touch sensing operation may be driven in close conjunction with each other. In one chip, information about a display driving frequency and information about driving time points may be transmitted and received through an interconnection included in the chip. Thus, connections between chips, which is required to transmit and receive the information, may be reduced or eliminated in a case in which a chip related to the display operation is provided separately from a chip related to the touch sensing operation. Furthermore, when the chips are separated from each other, the likelihood of defects may be increased due to errors in a timing fluctuate between oscillators embedded in respective chips. However, in the present embodiment, clock signals generated in the chips may be commonly used, and thus, the defects caused by errors between the chips may be reduced. Also, the embodiment may eliminate the need to define a specific interface protocol between two chips in advance.

Moreover, the above-described embodiment relates to a case where a time point at which touch data is generated is controlled based on a waveform of a voltage signal related to a display operation. However, embodiments are not limited thereto. In an operation example, a display panel may include a plurality of gate lines, and a distance by which a data signal is transmitted may differ according to a position of a driven gate line. That is, a capacitance component generated in a data transmission path may vary, and thus, a time point at which noise is generated may vary. That is, the time point at which the touch data is generated may fluctuate based on various operation states related to a display driving operation.

Figure 8:
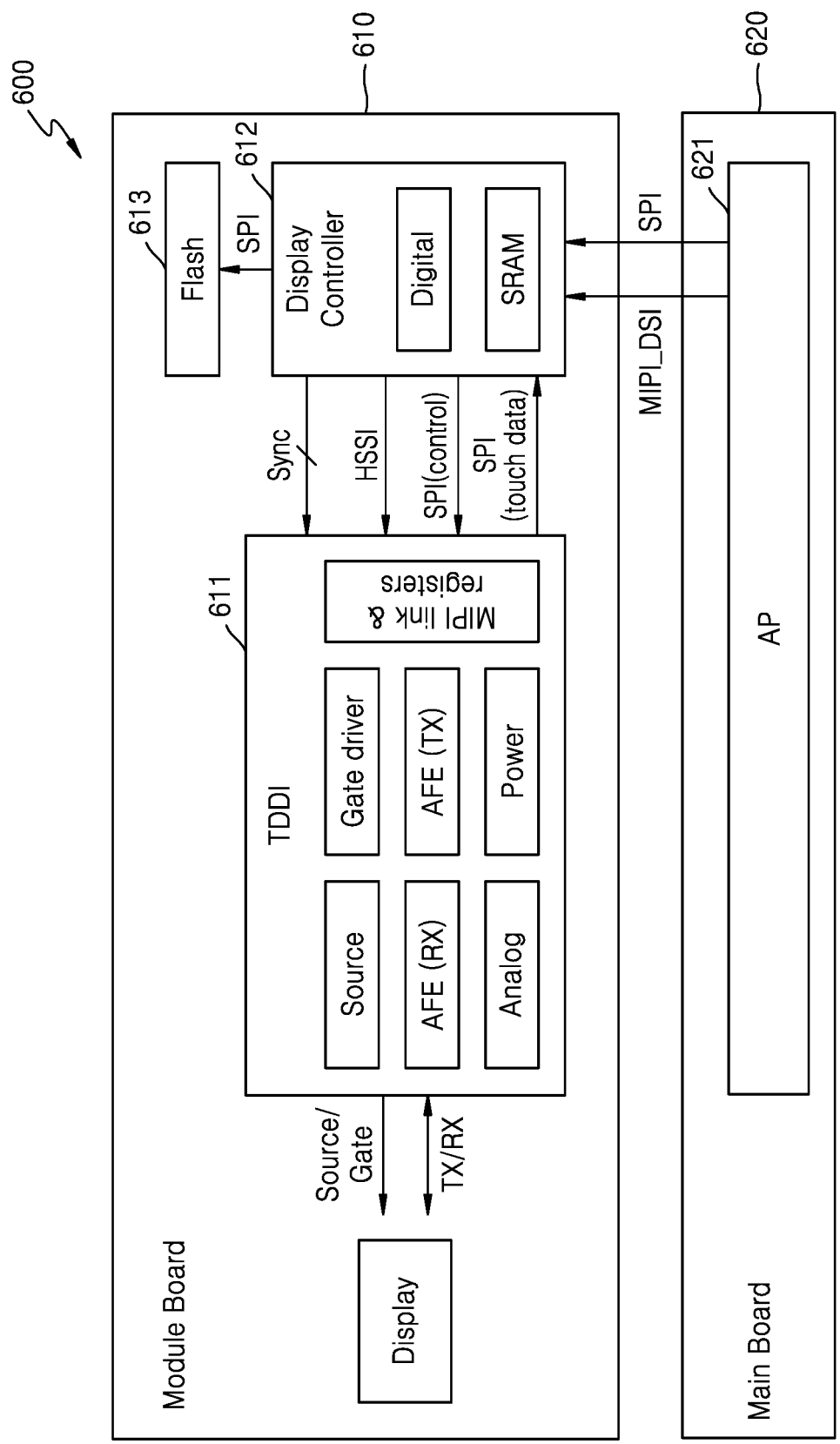
FIG. 8 is a block diagram illustrating a configuration of a display chipset included in a display system according to an example embodiment.

FIG. 8 is a block diagram illustrating an example of a configuration of a display chipset included in a display system 600 according to an example embodiment. FIG. 8 illustrates an example in which a display device includes a display panel and a touch panel, and is driven by a TDDI 611. The TDDI 611 may correspond to a configuration, which may mainly include analog circuits, from among various kinds of circuits configured to control a display operation and a touch sensing operation. Also, a display controller including various kinds of digital circuit blocks related to the display operation and the touch sensing operation may perform communications according to various kinds of interfaces.

Referring to FIG. 8, the display system 600 may include a module board 610 and a mainboard 620. The module board 610 may include a display disposed on the module board 610, a TDDI 611 and a display controller 612. The TDDI 611 and the display controller 612 are configured to drive the display device. Also, the module board 610 may include a flash memory 613 which may be located outside the display controller 612. The mainboard 620 may include an AP 621. The display controller 612 and the AP 621 may communicate with each other through various kinds of protocols (e.g., a mobile industry processor interface display serial interface (MIDI_DSI) and a serial peripheral interface (SPI)).

Functions of components of a display chipset structure shown in FIG. 8 will be described herein below.

The TDDI 611 may be implemented as a separate chip and may include various kinds of analog circuit blocks configured to drive the display device. For example, the TDDI 611 may drive a source line Source and a gate line Gate of the display device in relation to the display operation, and transmit a driving signal TX and receive a sensing signal RX in relation to the touch sensing operation. Here, the TDDI 611 may include a source driver, a gate driver, an AFE receiving block AFE (RX), an AFE transmission block AFE (TX), other analog circuit blocks, and a power generator (or a power controller). Also, the TDDI 611 may communicate with the display controller 612 and include an interface circuit (e.g., MIPI link & registers) configured to perform communications according to a predetermined interface. According to the above-described embodiments, the display controller 612 may include a memory (e.g., SRAM) and a digital circuit block.

The display controller 612 may include an interface circuit configured to communicate with the TDDI 611. Signals may be transmitted and received between the TDDI 611 and the display controller 612 according to various interfaces. As an example, various synchronous signals Sync may be provided to the TDDI 611. Also, various signals may be provided to the TDDI 611 according to a high-speed serial interface (HSSI), such as an MIPI, an embedded display port (eDP) interface, a low-voltage differential signaling (LVDS) interface, a universal serial interface module (USI-m) interface, a unified payment interface module (UPI-m) interface, and an enhanced reduced voltage differential signaling (eRVDS) interface. In addition, various pieces of control information may be provided by the display controller 612 to the TDDI 611 according to an SPI (control), and touch data may be provided by the TDDI 611 to the display controller 612 according to an SPI (touch data).

Based on the foregoing configuration, the display controller 612 may perform communication with each of a component driver chip and a host (AP 621) according to a predetermined interface. In an operation example, a first interface applied to communication between the display controller 612 and the component driver chip may be different from a second interface applied to communication between the display controller 612 and the host 621.

Figure 9:
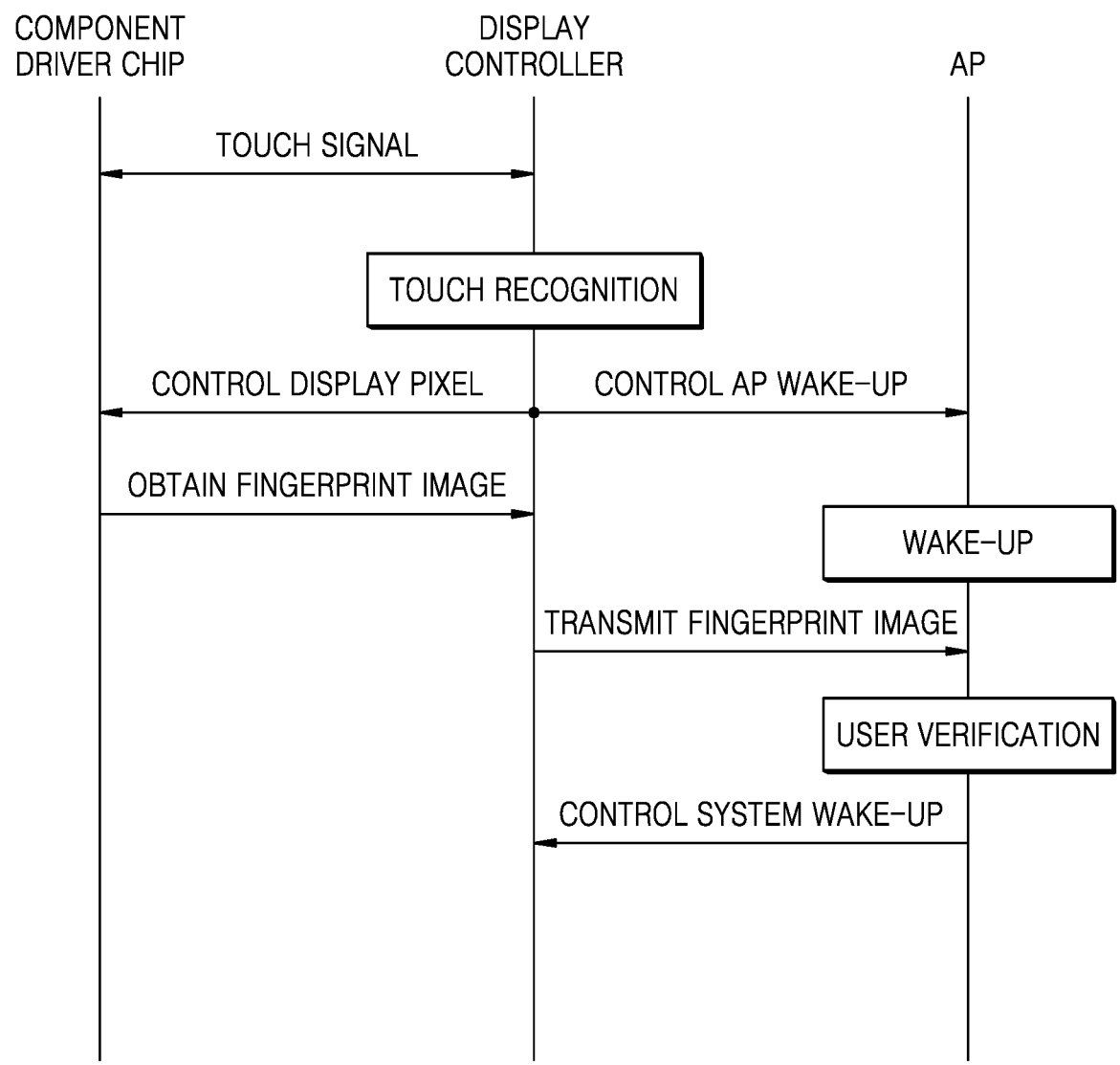
FIG. 9 is a flowchart illustrating an operation of a display system according to an example embodiment.
Figure 10:
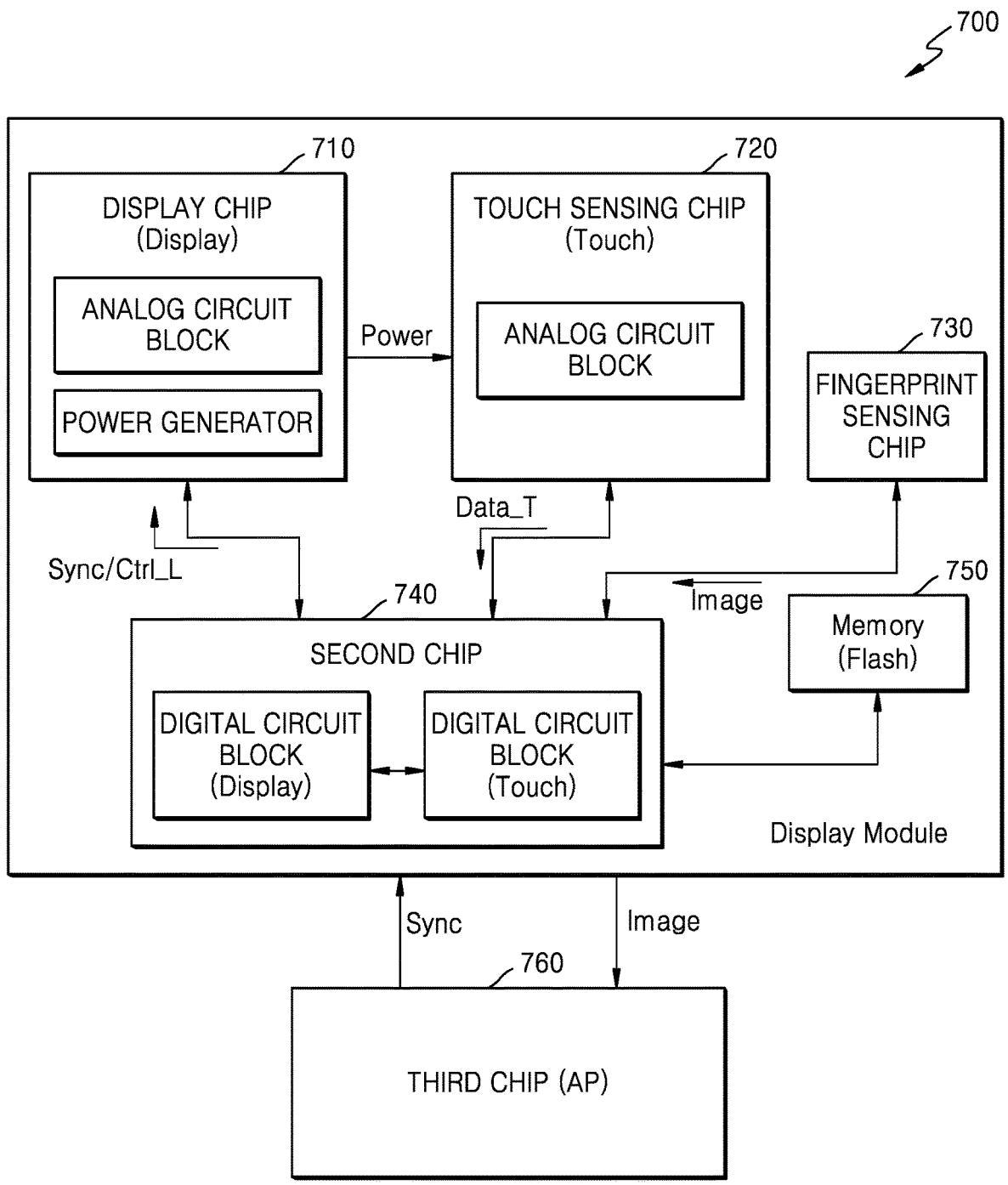
FIG. 10 is a diagram illustrating a display system according to an example embodiment.
Figure 11:
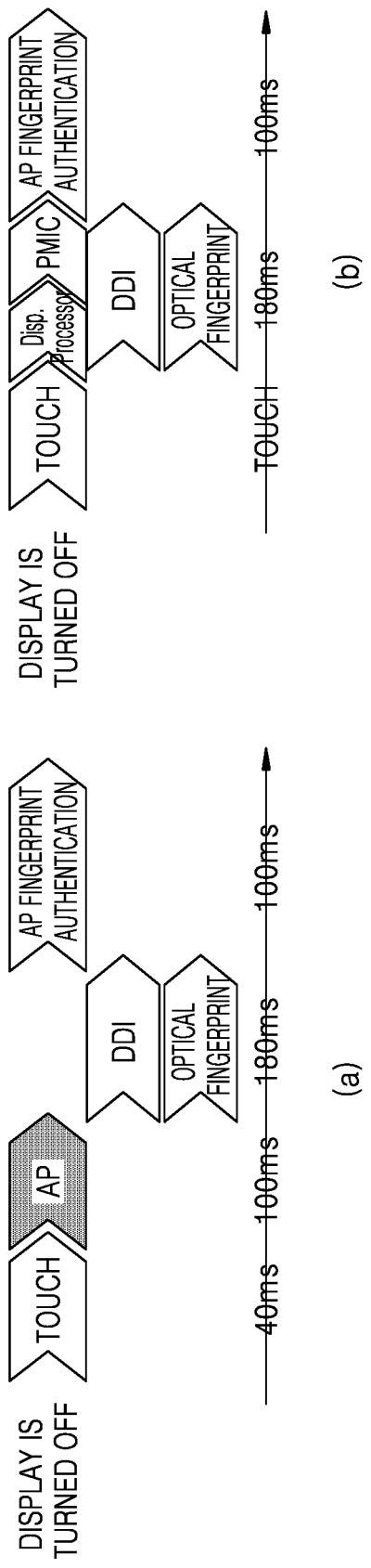
FIG. 11($a$) is a diagram illustrating an example operation of a display system in a related art.
Figure 12:
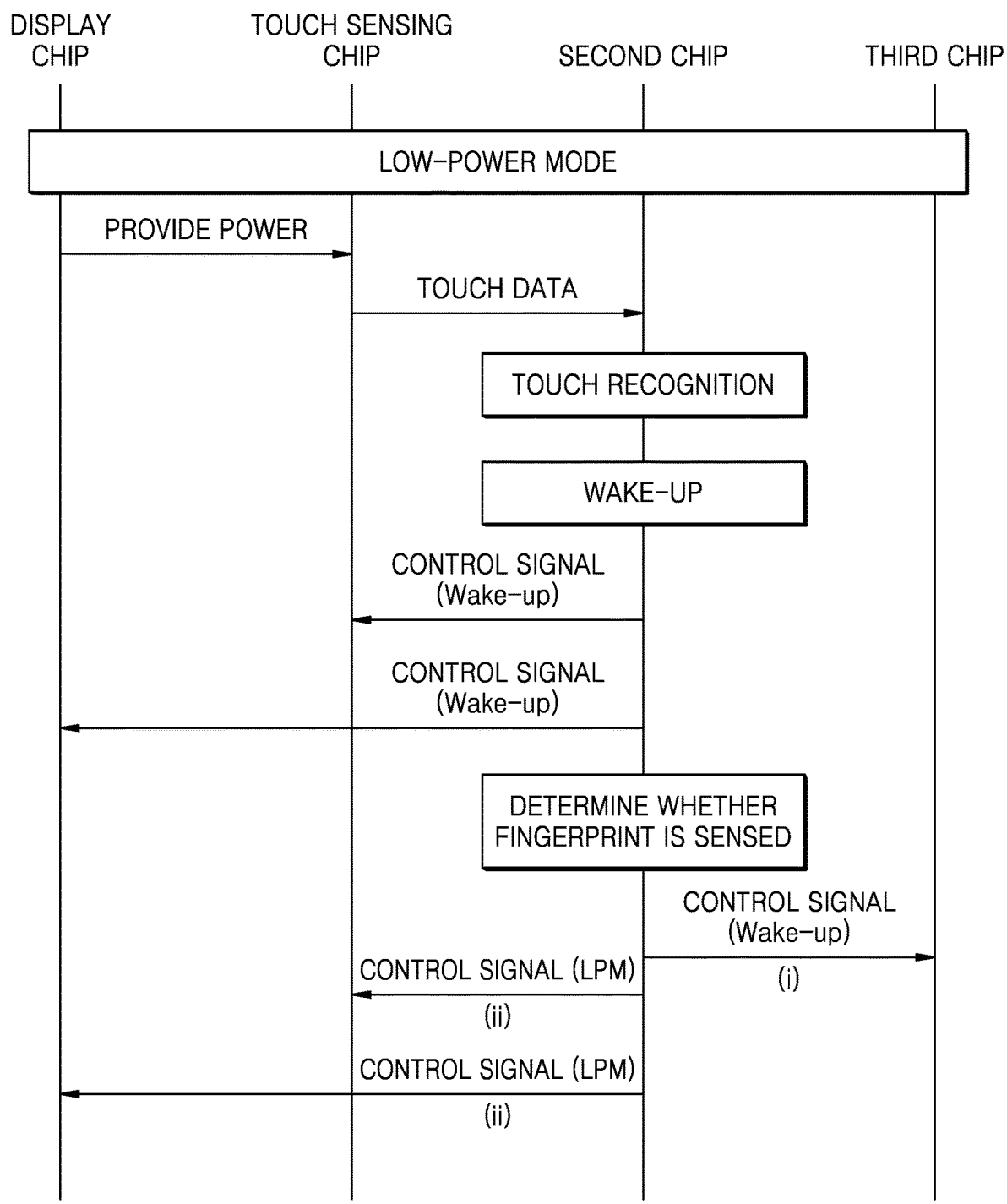
FIG. 12 is a flowchart illustrating an operation between components in a display system according to an example embodiment.

FIGS. 9 to 12 are diagrams illustrating operations of a display system 700 according to example embodiments. FIG. 9 is a flowchart illustrating an operation of a display system according to an example embodiment; FIG. 10 is a diagram illustrating a display system according to an example embodiment; FIG. 11(a) is a diagram illustrating an example operation of a display system in a related art; FIG. 11(b) is a diagram illustrating an example operation of a display system according to an example embodiment; and FIG. 12 is a flowchart illustrating an operation between components in a display system according to an example embodiment.

Referring to FIGS. 9 and 10, the display system 700 may include a plurality of first chips, which include a display chip 710 corresponding to a component driver chip of a display panel and a touch sensing chip 720 corresponding to a component driver chip of a touch panel. According to an embodiment, each of the display chip 710 and the touch sensing chip 720 may include an analog circuit block. For example, the display chip 710 of the first chip may further include a power generator configured to generate power for at least one of a display operation and a touch sensing operation. The display chip 710 may provide various kinds of synchronous signals Sync to the display panel. In an operation example, the synchronous signals Sync may be generated by an AP 760. In addition, the plurality of first chips may further include a fingerprint sensing chip 730 configured to provide a result obtained by sensing a user's fingerprint. When an optical fingerprint recognition method is applied, the fingerprint sensing chip 730 may include a photographing device configured to detect or capture an image of the user's fingerprint. However, the embodiment is not limited hereto. The plurality of first chips may include other chips corresponding to various component driver chip driving various functions of the display system 700.

Furthermore, the display system 700 may further include a second chip 740 corresponding to the display controller according to the above-described embodiments and at least one memory (e.g., a flash memory 750). The second chip 740 may include a digital circuit block related to the display operation and a digital circuit block related to the touch sensing operation.

When the display system 700 including the AP 760 enters a low-power mode and a display device of the display system 700 is turned off, the display device may be touched by a user, (e.g., touching with a finger). In this case, the user is authenticated by recognizing a fingerprint of the finger, a function of waking up the display system 700 (or a user device) may be triggered. In the above-described authentication operation, in typical scenario, after a touch by a user is recognized by a touch sensor and generated as a touch signal, a touch recognition result may be provided from a chip configured to control a touch operation to the AP. To control a series of operations including a display operation to enable fingerprint recognition, it may be necessary to perform a wake-up operation to convert the AP from the low-power mode to a normal mode.

In contrast, according to example embodiments, a series of processes for performing a fingerprint sensing operation may be performed under the control of the second chip 740 corresponding to the display controller. For example, touch data Data_T may be transmitted between the touch sensing chip 720 and the second chip 740, and the second chip 740 may provide a control signal Ctrl_L to the display chip 710 to acquire the user's fingerprint, and perform a control operation so that a display pixel may emit light. Also, the fingerprint sensing chip 730 may obtain a user's fingerprint image Image based on the light emitted by the display pixel. Further, the second chip 740 may perform a control operation for waking up the AP 760. The operation of controlling the display chip 710 and the touch sensing chip 720 of the first chip and the fingerprint sensing chip 730 to recognize the fingerprint and the operation of waking up the AP 760 may be performed in parallel, and thus, a required time may be greatly reduced as compared to a sequential processing method of the related art.

After the operation of waking up the AP 760, the second chip 740 may receive the fingerprint image Image from the fingerprint sensing chip 730 and transmit the fingerprint image Image to the AP 760. The AP 760 may perform a user verification process based on an operation of comparing the fingerprint image Image with a user's fingerprint that is previously stored. When the obtained fingerprint image Image corresponds to a fingerprint of a user who has a use authority, the AP 760 may provide a control signal for entirely waking up the display system 700 to the second chip 740.

Moreover, in the above-described embodiment, only a partial region of the display panel may selectively emit light in relation to the fingerprint recognition operation, and the second chip 740 corresponding to the display controller may provide information about an emission region used for the fingerprint recognition operation. Also, fingerprint information that is previously registered by the user may be stored in a predetermined memory. When the second chip 740 receives the registered fingerprint information, the second chip 740 may perform a fingerprint matching operation and perform an authentication operation based on the matching result.

FIG. 11(*a*) is a diagram illustrating an example of a time required for a fingerprint authentication operation according to the related art and FIG. 11(*b*) is a diagram illustrating an example of a time required for a fingerprint authentication operation according to an example embodiment. According to the above-described example embodiment, the display controller may serve as a local host of the display system 700, and thus, the operation of waking up the AP 760 and the operation of obtaining the fingerprint image may be simultaneously performed. Thus, a time taken from the start of the touch recognition operation to the end of the fingerprint authentication operation may be greatly reduced. As a result, the sensitivity of an optical fingerprint sensor may be improved.

FIG. 12 is a flowchart illustrating various modes and operation examples of a communication between the display chip 710 and the touch sensing chip 720 of the first chip, the second chip 740 corresponding to the display controller, and the third chip 760 (also, "the AP 760").

For example, when the display system 700 is in a low-power mode (LPM), each of the display chip 710 and the touch sensing chip 720 of the first chip, the second chip 740, and the AP 760 may enter the low-power mode. The display chip 710 may include a power generator configured to generate power related to the display operation and power related to the touch sensing operation, and provide power to the touch sensing chip 720 to periodically or aperiodically sense a touch or a non-touch in the low-power mode. Also, the touch sensing chip 720 may generate touch data using a sensing signal from a sensing electrode of the touch panel and provide the touch data to the second chip 740. In addition, the second chip 740 may provide the touch data from the touch sensing chip 720 to the AP 760.

Moreover, the second chip 740 may recognize a touch based on received touch data, and the second chip 740 may fluctuate in a wake-up state to subsequently perform a series of operations. Also, before waking up the AP 760, the second chip 740 may transmit a control signal for waking up the display chip 710 and the touch sensing chip 720 of the first chip.

Furthermore, the second chip 740 may determine whether the touch operation is a touch for a fingerprint sensing operation, and control subsequent operations based on the determination result. As an example, when the touch operation is the touch for the fingerprint sensing operation, the second chip 740 may wake up the fingerprint sensing chip 730 for obtaining a fingerprint image and output a control signal for waking up the AP 760 (Step (i)). In contrast, when the touch operation is not the touch for the fingerprint sensing operation, the second chip 740 may transmit a control signal for enabling the display chip 710 and the touch sensing chip 720 of the first chip to enter the low-power mode again (Step (ii)). That is, when the touch operation is not the touch for the fingerprint sensing, the AP 760, which requires high power consumption, is not awaken, therefore, the entire power consumption of the display system 700 may be reduced.

According to another operation example, when the display system 700 is in the low-power mode (LPM) in which the display device is turned off, the above-described touch sensing operation may be periodically performed, and it may be determined whether the touch operation is the touch for the fingerprint sensing operation. In this case, when the touch operation is not related to the fingerprint sensing operation, the second chip 740 controls the first chip including the display chip 710 and the touch sensing chip 720 in the low-power mode without waking up the display chip 710 and the touch sensing chip 720 of the first chip.

Figure 13:
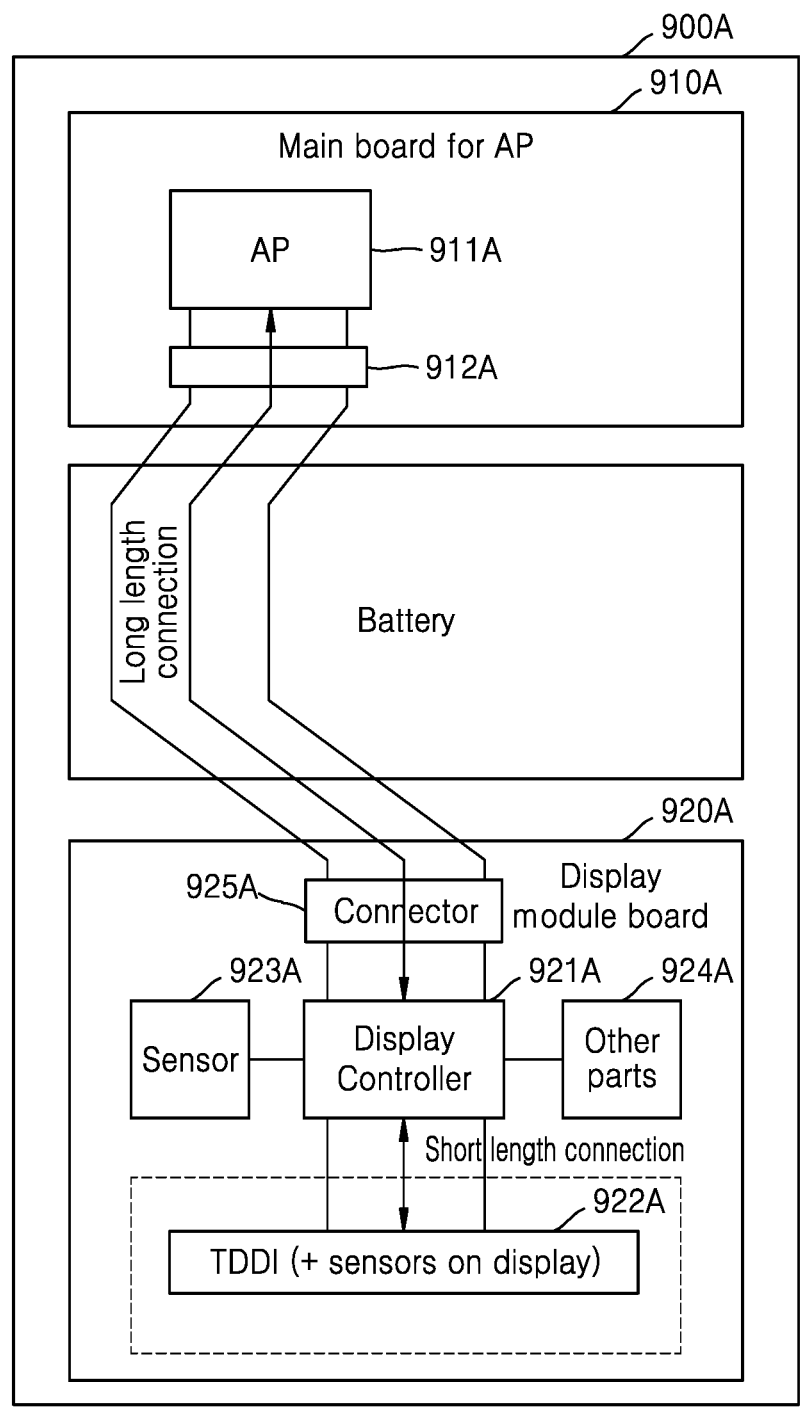
FIGS. 13 and 14 are diagrams illustrating examples of a mobile device corresponding to a display system according to example embodiments.
Figure 14:
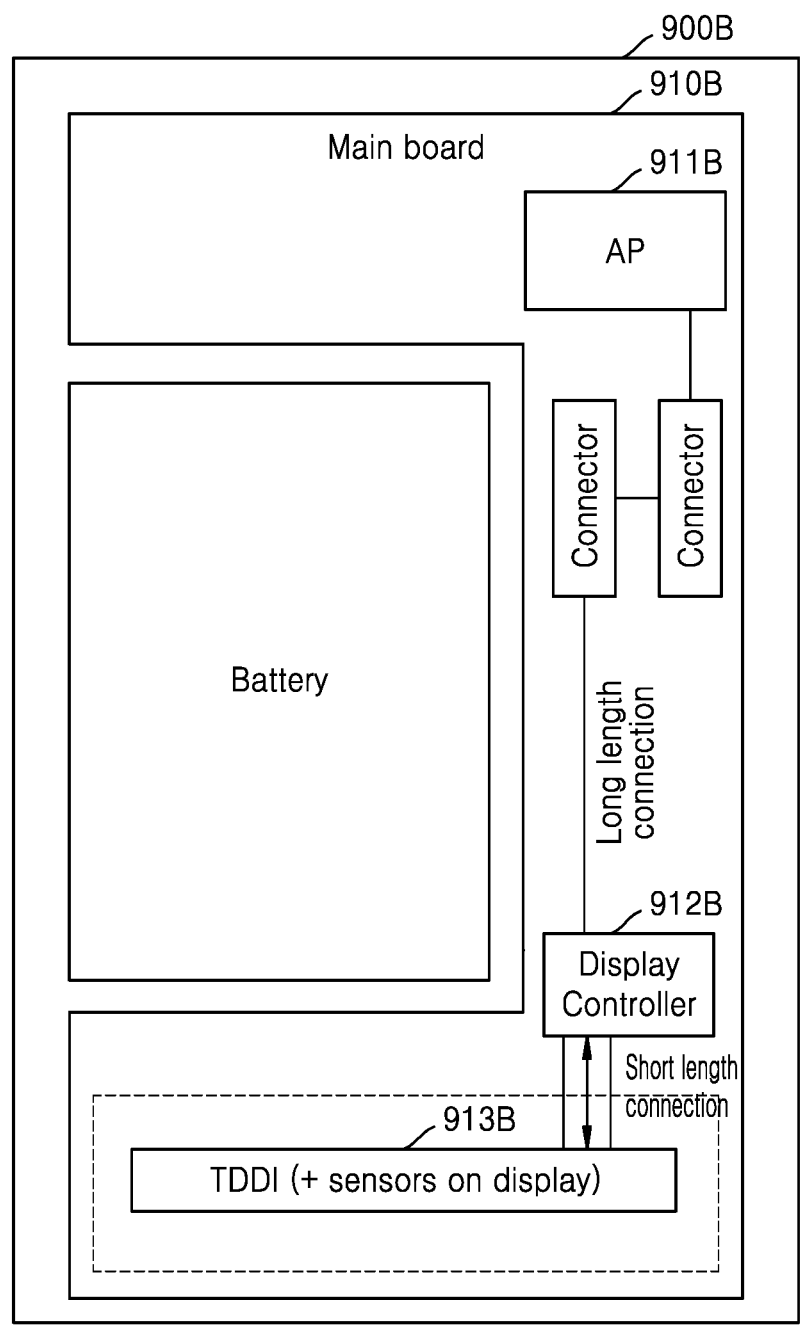

FIGS. 13 and 14 are diagrams illustrating examples of a mobile device corresponding to a display system according to example embodiments.

The latest mobile devices are configured to save up the largest possible battery space in order to maximize the operating time of the mobile device. Accordingly, a board configuration may be separated into boards located at upper and lower ends to save up space for a battery. That is, main components (e.g., an AP, a radio-frequency (RF) device, and a camera) may be designed on one board, and a universal serial bus (USB) and an external connection component for a display device may be designed on another board.

For example, as shown in FIG. 13, a mobile device 900A may include one board (e.g., a mainboard 910A) and another board (e.g., a display module board 920A). A display controller 921A and a TDDI 922A may be configured on the display module board 920A and very tightly connected to each other. Short connection between the display controller 921A and the TDDI 922A may lead to improvements in channel characteristics of an interface between the display controller 921A and the TDDI 922A. Thus, power consumption of the interface may be reduced, and additional characteristics, such as electromagnetic interference (EMI), may also be improved. That is, as shown in FIG. 13, the display controller 921A may be configured on the display module board 920A. Thus, the display controller 921A and the TDDI 922A may be closely located to each other, compared to a configuration between an AP 911A and the display controller 921A. As a result, signal characteristics may be enhanced. In other words, a distance between the display controller 921A and the TDDI 922A may be significantly shorter than a distance between the AP 911A and the display controller 921A.

As shown in FIG. 13, a connector 912A of the mainboard 910A may be connected to a connector 925A of the display module board 920A, and other components (e.g., at least one sensor 923A) and other parts 924A may be disposed on the display module board 920A.

In a case in which an arrangement of components is different from the arrangement of FIG. 13, an L-shaped display module board may be provided. In this case, a display controller may be disposed on a display module board, and an interface between the display controller and a TDDI may have a shorter length than an interface between an AP and the display controller. Thus, design requirements of a high-speed interface for a display may be alleviated. That is, power consumed by an interface IP may be reduced. Also, the L-shaped display module board may extend a battery space by appropriate arrangement of the display controller. For example, according to an embodiment shown in FIG. 14, a mobile device 900B may include an L-shaped mainboard 910B. An AP 911B may be arranged on one side of the mainboard 910B, a display controller 912B and a TDDI 913B may be arranged on another side of the mainboard 910B, and the AP 911B may be connected to the display controller 912B through at least one connector.

Furthermore, embodiments may be applied to the following systems or devices. As an example, the embodiments may be applied to a display system on which a display and a touch sensor are mounted, a display system on which a display and a fingerprint sensor are mounted, a display system on which a display and a bio-sensor are mounted, and a display system on which a display and two or three of the touch sensor, the fingerprint sensor, and the bio-sensor are mounted. Also, the embodiments may be applied to a mobile device, a tablet, a note PC, a television (TV), and an arbitrary display device on which the display system is mounted.

According to the embodiments, a touch screen or another display component may be used together in addition to a display, and each component may operate in conjunction with the display. Also, a component configured to integrate and manage display components and a main system processor may be provided between the display components and the main system processor. As an example, a triple structure including an AP, a display controller, and a driver/sensor may be provided. Furthermore, all or some of the display controller and the respective components may be connected in a star form.

Figure 15:
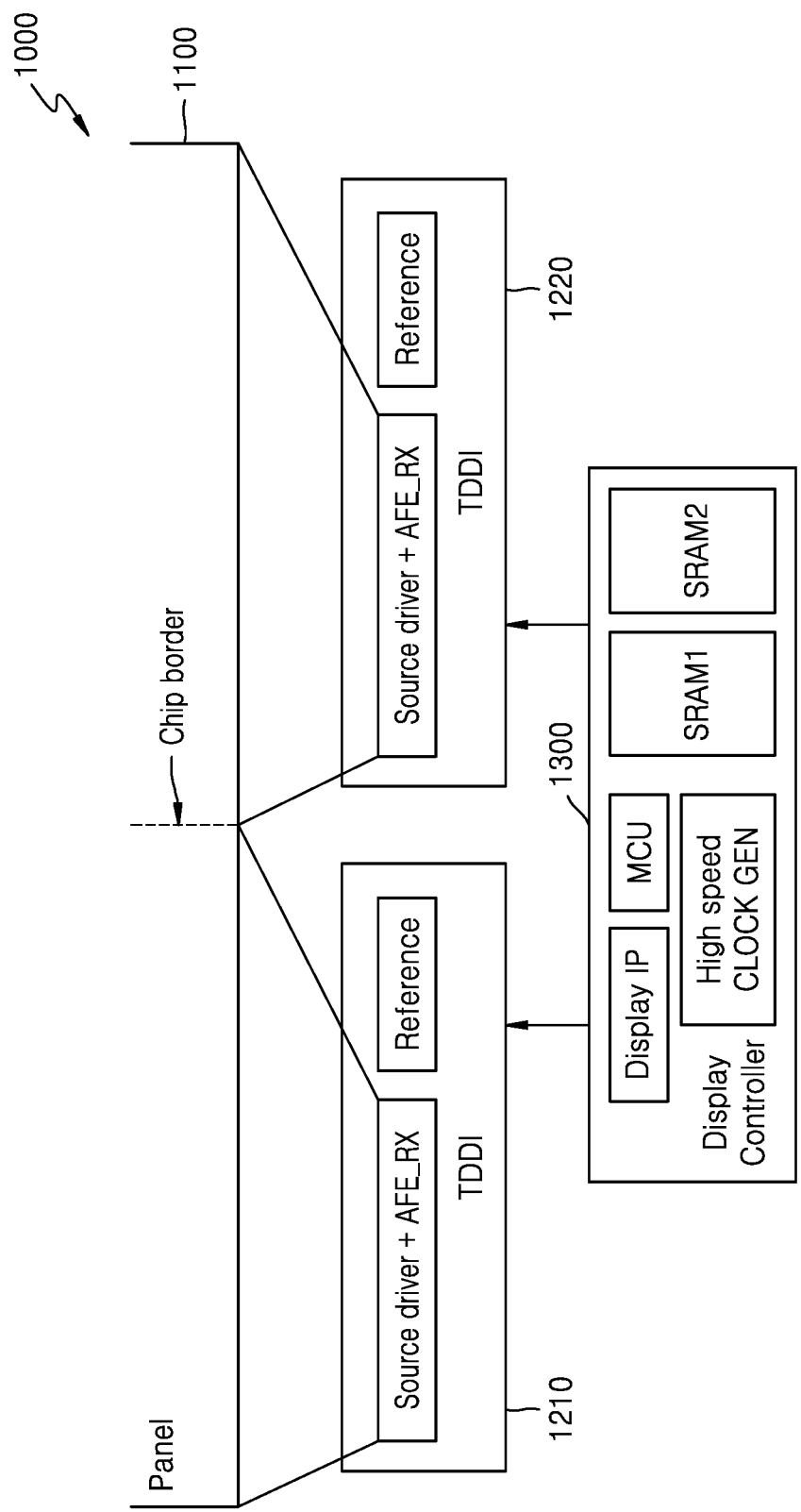
FIG. 15 is a block diagram illustrating a display system according to another example embodiment.

FIG. 15 is a block diagram of a display system 1000 according various embodiments.

As shown in FIG. 15, the display system 1000 may include at least one panel (e.g., display panel), and a plurality of analog chips may be disposed to correspond to one panel 1100. Although two TDDIs 1210 and 1220 are illustrated in FIG. 15, the embodiment is not limited thereto. There may be more than two TDDIs. Also, each of the TDDIs 1210 and 1220 may include analog circuits related to a display operation and a touch sensing operation. Any one of the TDDIs 1210 and 1220 may drive a partial region of the display panel. As an example, a panel may be divided into a plurality of regions based on boundaries corresponding to chips. In FIG. 15, a block denoted by Reference may be a component configured to provide various reference signals, such as a reference current and a reference voltage.

In addition, a display controller 1300 may be provided to control to the TDDIs 1210 and 1220. In the related art, when a plurality of chips are arranged as described above, errors may occur during the calculation of touch coordinates at boundary regions between the chips, and additional interconnections and circuits may be needed to prevent the occurrence of such errors. In contrast, according to the present embodiment, an operation of processing data of the entire screen region and an operation of controlling time points may be performed by one chip (i.e., one display controller 1300), and thus, the occurrence of errors may be reduced.

Figure 16:
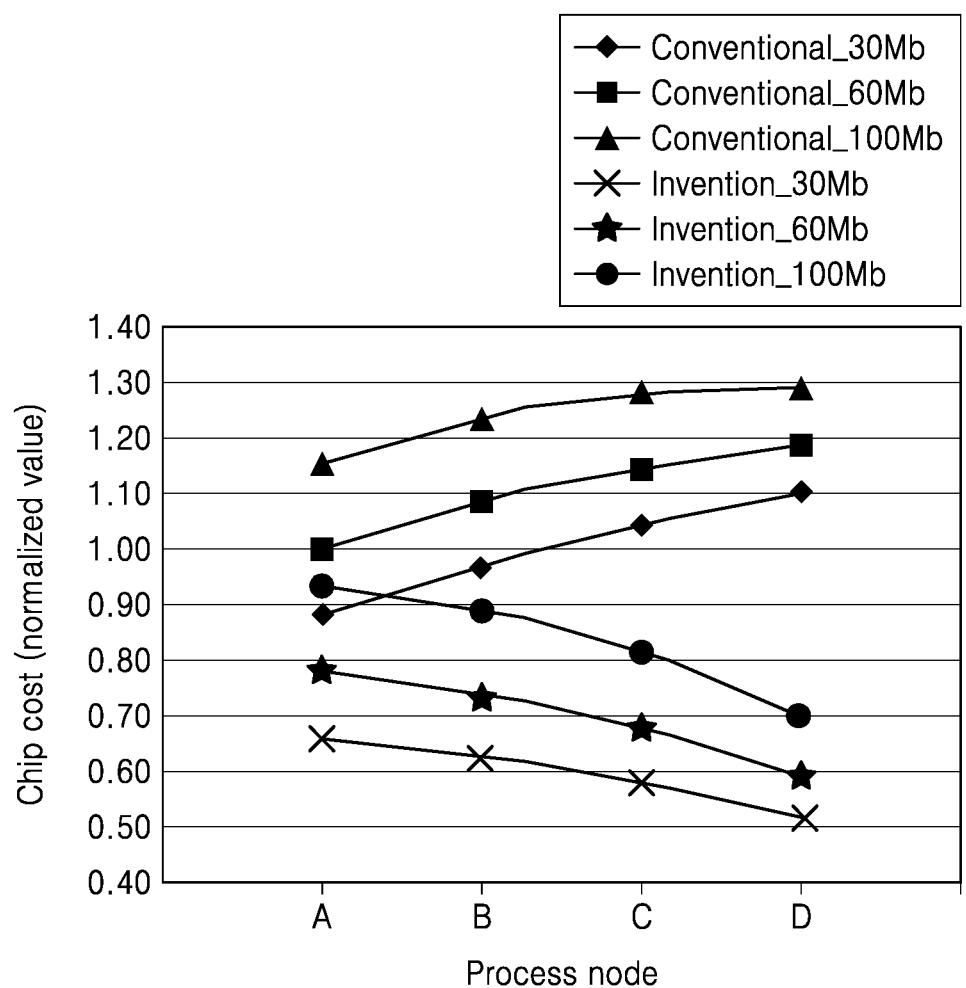
FIG. 16 is a graph showing an effect of reducing chip costs according to various embodiments.

FIG. 16 is a graph showing an effect of reducing chip costs according to various embodiments.

According to the above-described embodiments, manufacturing costs may be reduced due to process shrinkage. As an example, a method of reducing process costs due to the process shrinkage may be one of the most effective ways to reduce chip costs. However, in the case of a DDI in which analog circuits make up a large portion of a chip, a cost reduction effect due to the process shrinkage may not be significant.

In contrast, according to embodiments, a cost reduction due to process shrinkage may be enhanced. FIG. 16 illustrates an example of cost per chip according to the related arts and the present embodiments. The graph of FIG. 16 may be calculated through a predetermined formula into which a chip area, the number of masks, and the selection of a fabrication process are input. Also, FIG. 16 illustrates an example in which cost is calculated for each size of a memory included in a chip.

In a DDI chip of the related art, it can be seen that chip costs increase when process shrinkage is applied for the same logic and memory size. Manufacturing cost per unit area of a wafer may be increased due to the process shrinkage. However, since an analog circuit, which makes up at least half of a chip, does not benefit from an area reduction due to the application of leading-edge processes, the chip cost may be increased as much as an increase in the manufacturing cost. In contrast, when a digital circuit is separated from an analog circuit and a low-cost process is applied to the analog circuit, an increase in manufacturing cost due to the analog circuit may not occur, and the digital circuit may obtain a chip cost reduction effect due to process shrinkage. As a result, an integrated display chipset structure according to the embodiments described herein may effectively reduce chip manufacturing costs by using the process shrinkage.

While the embodiments of the disclosure have been specifically shown and described, it will be understood that various changes in form and details may be made therein without departing from the spirit and scope of the following claims.

What is claimed is:

1. A display controller comprising:
a display processor comprising a first digital circuit, and configured to receive image data from an application processor (AP) and output the image data to a first component driver chip configured to drive a gate line and a source line of a display panel; and
a touch processor comprising a second digital circuit, and configured to receive touch data from a second component driver chip configured to drive sensing electrodes of a touch panel,
wherein the display controller is implemented as one semiconductor chip and separated from each of the first component driver chip and the second component driver chip,
wherein the display processor and the touch processor communicate with each other through an internal interconnection of the one semiconductor chip, and
wherein the display processor comprises:
a frame memory configured to store the image data to be displayed on the display panel; and
an image processing circuit configured to perform an image processing operation on the image data.

2. The display controller of claim 1, wherein the display processor further comprises a timing controller configured to output one or more synchronous signals to the first component driver chip, and
wherein timing information based on at least one synchronous signal among the one or more synchronous signals is provided to the touch processor.

3. The display controller of claim 2, wherein the touch processor is further configured to generate a timing control signal based on the timing information, and transmit the timing control signal to the second component driver chip to control a time point at which the touch data is generated.

4. The display controller of claim 1, further comprising a fingerprint processor comprising a third digital circuit configured to perform a fingerprint recognition function, the fingerprint processor being configured to control a third component driver chip to generate a fingerprint image and configured to drive a fingerprint sensor.

5. The display controller of claim 1, further comprising a bio-signal processor comprising a fourth digital circuit configured to perform a bio-signal sensing function, the bio-signal processor being configured to control a sensing operation of a fourth component driver chip, wherein the fourth component driver chip is configured to drive a bio-signal sensor.

6. The display controller of claim 1 wherein the display processor is configured to transmit a control signal to the first component driver chip when the first component driver chip is in a low-power mode, and
wherein a power generator included in the first component driver chip supplies power to the second component driver chip to periodically perform a touch sensing operation.

7. The display controller of claim 1, wherein the touch processor further comprises:
a memory configured to store the touch data received from the second component driver chip; and
a touch position calculator configured to calculate a touch position based on information stored in the memory.

8. A method of operating a display controller, the method comprising:
receiving, by a second digital circuit included in the display controller, touch data obtained from a second component driver chip and controlling the second component driver chip to drive sensing electrodes of a touch panel;
controlling, by a first digital circuit included in the display controller, a first component driver chip to drive a pixel of a display panel for a fingerprint sensing operation;
receiving a fingerprint image from a third component driver chip that is configured to drive a fingerprint sensor;
transmitting a first control signal for waking up an application processor (AP) that is in a low-power mode, to the application processor; and
transmitting the fingerprint image to the application processor for a fingerprint authentication operation,
wherein the display controller is implemented as one semiconductor chip and separated from each of the first component driver chip, the second component driver chip and the third component driver chip.

9. The method of claim 8, wherein the first component driver chip and the second component driver chip are in a low-power mode,
the method further comprising outputting a second control signal for waking up the first component driver chip and the second component driver chip based on the received touch data.

10. The method of claim 8, further comprising determining whether the touch data indicates a touch of a user for the fingerprint sensing operation,
wherein the transmitting the first control signal to the application processor further comprises selectively transmitting the first control signal based on the touch data indicating the touch of the user for the fingerprint sensing operation.

11. The method of claim 10, further comprising:
outputting a third control signal configured to drive the first component driver chip and the second component driver chip to enter the low-power mode based on determining that the touch data does not indicate the touch of the user for the fingerprint sensing operation.

12. The method of claim 8, further comprising:
transmitting at least one piece of timing information related to a display operation from the first digital circuit to the second digital circuit; and
outputting, from the second digital circuit, a timing control signal for controlling a time point at which the touch data is generated by the second component driver chip.

13. The method of claim 8, further comprising:
communicating with the first component driver chip and the second component driver chip according to a first interface; and communicating with the application processor according to a second interface, wherein the first interface is different from the second interface.

14. A display system comprising:
a display panel;
a touch panel;
a plurality of component driver circuits comprising a display driver configured to drive the display panel and a touch controller configured to drive the touch panel, the display driver and the touch controller including analog circuits; and
a display controller implemented as a separate chip between the plurality of component driver circuits and an application processor (AP), the display controller comprising a first digital circuit configured to control the display driver and a second digital circuit configured to control the touch controller,
wherein the display controller is configured to transmit image data for displaying an image on the display panel to a source driver included in the display driver.

15. The display system of claim 14, wherein the display controller is further configured to receive touch data from the touch controller comprising an analog front end (AFE), wherein the touch data is based on a result of the driving of the touch panel.

16. The display system of claim 14, wherein the first digital circuit is configured to transmit at least one piece of timing information related to a display operation to the second digital circuit, and wherein the second digital circuit is configured to generate a timing control signal for controlling a time point at which touch data is generated by the touch controller.

17. The display system of claim 14, further comprising a mainboard and a display module board, wherein the application processor is mounted on the mainboard, and the plurality of component driver circuits and the display controller are mounted on the display module board.

18. The display system of claim 14, wherein the display driver comprises a power generator configured to generate power for a display operation and a touch sensing operation, and wherein, when the display driver is in a low-power mode, the power generator provides power to the touch controller so that the touch controller periodically performs the touch sensing operation.

19. The display system of claim 14, further comprising a fingerprint sensor, wherein the plurality of component driver circuits further comprise a fingerprint controller configured to drive the fingerprint sensor, and the display controller further comprises a third digital circuit configured to control the fingerprint controller, and wherein the display controller controls an operation of generating a fingerprint image without waking up the application processor that is in a low-power mode.

* * * * *